United States Patent
Ohuchi et al.

(10) Patent No.: US 8,055,040 B2
(45) Date of Patent: Nov. 8, 2011

(54) ULTRASONIC IMAGE PROCESSING APPARATUS AND METHOD FOR PROCESSING ULTRASONIC IMAGE

(75) Inventors: Hiroyuki Ohuchi, Nasushiobara (JP); Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 786 days.

(21) Appl. No.: 12/144,047

(22) Filed: Jun. 23, 2008

(65) Prior Publication Data
US 2008/0317316 A1 Dec. 25, 2008

(30) Foreign Application Priority Data
Jun. 25, 2007 (JP) ................. 2007-166851

(51) Int. Cl.
*G06K 9/62* (2006.01)
(52) U.S. Cl. ........................ 382/128; 600/463
(58) Field of Classification Search .................. 382/128; 600/437–461
See application file for complete search history.

(56) References Cited

U.S. PATENT DOCUMENTS

| | | | |
|---|---|---|---|
| 5,860,927 A * | 1/1999 | Sakaguchi et al. | 600/453 |
| 6,638,221 B2 | 10/2003 | Abe et al. | |
| 7,824,337 B2 * | 11/2010 | Abe et al. | 600/441 |
| 2004/0247165 A1 * | 12/2004 | Nishiura | 382/128 |
| 2006/0004291 A1 * | 1/2006 | Heimdal et al. | 600/459 |

FOREIGN PATENT DOCUMENTS
JP 2003-175041 6/2003
* cited by examiner

*Primary Examiner* — Hoon Song
(74) *Attorney, Agent, or Firm* — Oblon, Spivak, McClelland, Maier & Neustadt, L.L.P.

(57) ABSTRACT

Obtains the position of each of points composing the contour of a specific tissue shown in ultrasonic image data having been acquired at each time phase by pattern matching for each time phase. Obtains motion information of each of parts composing the specific tissue based on the position of each of the points composing the contour. For each time phase, obtain the differential value of the motion information of each of the parts by differentiating the motion information of each of the parts by time, and normalizes the differential value of the motion information. Assigns a color corresponding to the magnitude of the normalized differential value of the motion information to each of the parts displays an ultrasonic image at each time phase and furthermore display each of the parts of the specific tissue shown in the ultrasonic image of each time phase in the assign color.

7 Claims, 9 Drawing Sheets

ULTRASONIC IMAGE PROCESSING APPARATUS AND METHOD FOR PROCESSING ULTRASONIC IMAGE

BACKGROUND OF THE INVENTION

1. Field of the Invention

The present invention relates to an ultrasonic image processing apparatus configured to obtain the motion state of a subject by using an ultrasonic image of the subject acquired with ultrasonic waves, and a method for processing an ultrasonic image.

2. Description of the Related Art

It is extremely important to objectively and quantitatively evaluate the functions of living body tissues such as the myocardium of a heart, for diagnosis of the living tissues. A quantitative evaluation method based on image data of a heart acquired using an ultrasonic imaging apparatus has been proposed.

For example, a method of obtaining motion information such as displacement and strain of a tissue by tracking the speckle pattern of images has been proposed (Japanese Unexamined Patent Application Publication No. 2003-175041). This method, in which pattern matching is performed by using the speckle pattern of images, is referred to as Speckle Tracking (ST). Hereinafter, this method may be referred to as the ST method.

For specific example, in the case of evaluation of the myocardium of a heart, tomographic image data is acquired for each cardiac phase by transmitting ultrasonic waves to the heart. Then, by performing pattern matching by speckle tracking, it is possible to obtain the displacement of the endocardium and the displacement of the epicardium for each cardiac phase.

Then, it is possible to obtain the strain of the myocardium at each time phase based on the displacement of the endocardium and the displacement of the epicardium at each cardiac phase, and furthermore, it is possible to obtain the strain rate indicating the temporal change rate of strain.

This strain rate is a value corresponding to the speed of the heart during expansion. A higher strain rate indicates that a diastolic function is normal. Therefore, the strain rate is used as one index for evaluation of a diastolic function. As described above, evaluation of a heart is performed by obtaining wall-motion information such as displacement, strain and strain rate. Further, it is possible to perform evaluation of a heart by obtaining information such as rotation and twist of the myocardium as wall-motion information.

However, even if the heart is healthy, there may be variations in absolute value of strain depending on cardiac phases. In this case, the variations also affect the strain rate obtained from the strain. Likewise, there may be variations in absolute value of rotation or twist of the myocardium. Therefore, it has been difficult to appropriately evaluate the diastolic function of each part of the myocardium by an evaluation method using the absolute values of wall-motion information such as strain rate.

SUMMARY OF THE INVENTION

An object of the present invention is to provide an ultrasonic image processing apparatus that provides information used in evaluation of the motion state of a specific tissue while reducing the influence of variations in motion information in the specific tissue, and also provide a method for processing an ultrasonic image.

In a first aspect of the present invention, an ultrasonic image processing apparatus comprises: a contour tracking part configured to receive ultrasonic image data acquired at each time phase by scanning a subject with ultrasonic waves, further receive designation of a contour of a specific tissue shown in an ultrasonic image based on ultrasonic image data acquired at an arbitrary time phase, and obtain a position of each of points composing the contour of the specific tissue in the ultrasonic image data acquired at the each time phase by pattern matching at each time phase based on the ultrasonic image data acquired at the each time phase; a computing part configured to obtain motion information of each of parts composing the specific tissue at each time phase based on the position of each of the points composing the contour, obtain a differential value of the motion information of each of the parts at each time phase by differentiating the motion information of each of the parts with respect to time, divide the differential value of the motion information at each of the parts by a maximum value of an absolute value of the motion information at each of the parts to obtain a normalized differential value of the motion information at each of the parts at each time phase, and assign a color corresponding to a magnitude of the normalized differential value of the motion information to each of the parts; and a display controller configured to control a display device to display an ultrasonic image based on the ultrasonic image data acquired at the each time phase, and further control to display each of the parts of the specific tissue shown in the ultrasonic image of the each time phase in a color assigned to each of the parts.

According to the first aspect, it becomes possible to reduce the influence of variations in absolute value of wall-motion information by normalizing the differential value of the wall-motion information by the maximum value of the absolute value of the wall-motion information. Consequently, it becomes possible to appropriately provide information used in evaluation of the motion state of a specific tissue.

Further, in a second aspect of the present invention, a method for processing an ultrasonic image comprises: acquiring ultrasonic image data acquired at each time phase by scanning a subject with ultrasonic waves; receiving designation of a contour of a specific tissue shown in an ultrasonic image based on ultrasonic image data acquired at an arbitrary time phase, and obtaining a position of each of points composing the contour of the specific tissue in the ultrasonic image data acquired at the each time phase by pattern matching at each time phase based on the ultrasonic image data acquired at the each time phase; obtaining motion information of each of parts composing the specific tissue at each time phase based on the position of each of the points composing the contour; obtaining a differential value of the motion information of each of the parts at each time phase by differentiating the motion information of each of the parts with respect to time; dividing the differential value of the motion information at each of the parts by a maximum value of an absolute value of the motion information at each of the parts to obtain a normalized differential value of the motion information at each of the parts at each time phase; assigning a color corresponding to a magnitude of the normalized differential value of the motion information to each of the parts; displaying an ultrasonic image based on the ultrasonic image data acquired at the each time phase; and displaying each of the parts of the specific tissue shown in the ultrasonic image of the each time phase in a color assigned to each of the parts.

DETAILED DESCRIPTION OF THE EMBODIMENTS

Figure 1:
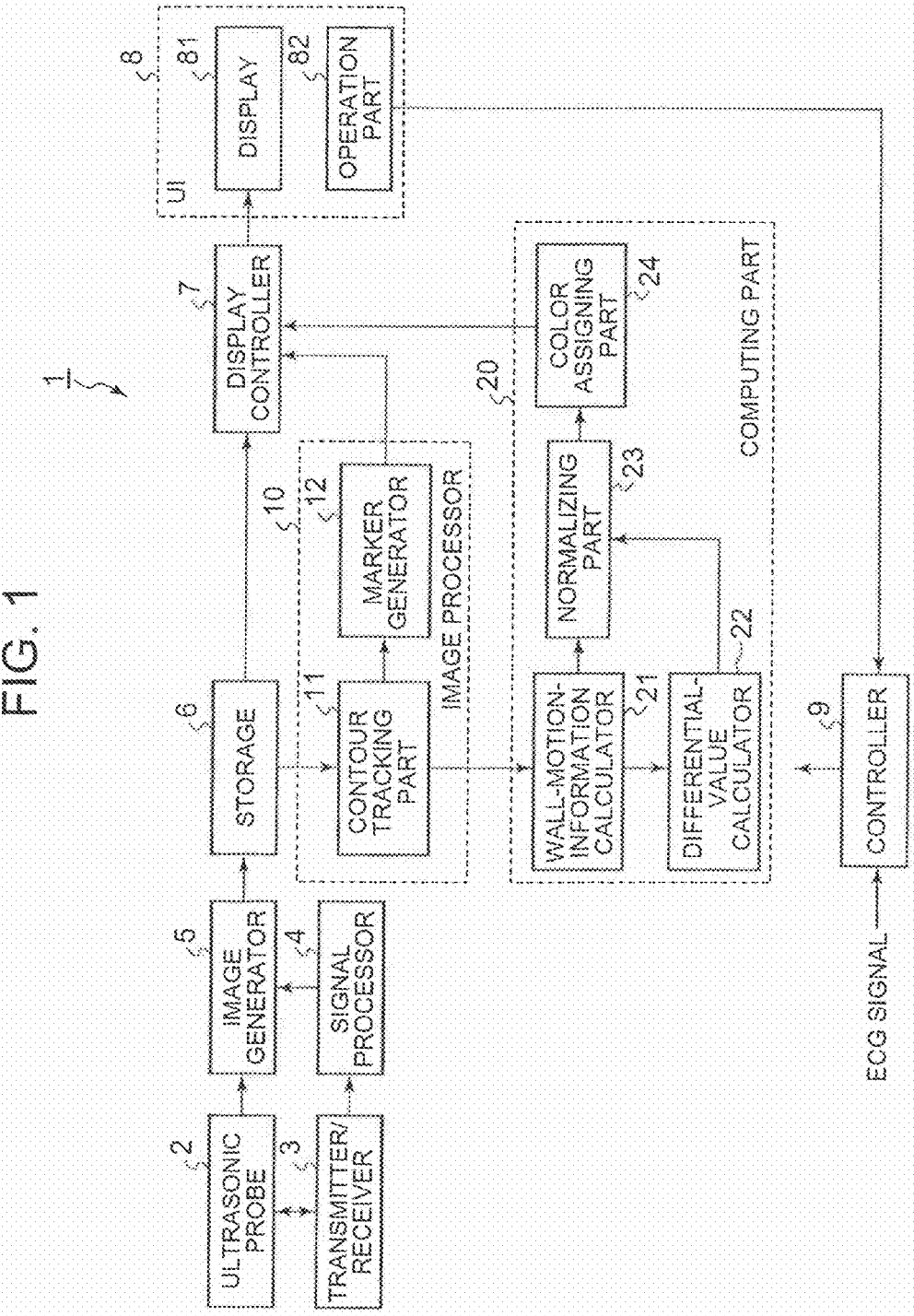
FIG. 1 is a block diagram showing an ultrasonic imaging apparatus according to an embodiment of the present invention.

An ultrasonic imaging apparatus according to an embodiment of the present invention will be described referring to FIG. 1. FIG. 1 is a block diagram showing the ultrasonic imaging apparatus according to the embodiment of the present invention.

An ultrasonic imaging apparatus 1 comprises an ultrasonic probe 2, a transmitter/receiver 3, a signal processor 4, an image generator 5, a storage 6, a display controller 7, a user interface (UI) 8, a controller 9, an image processor 10, and a computing part 20. The storage 6, the display controller 7, the user interface (UI) 8, the image processor 10 and the computing part 20 configure an ultrasonic image processing apparatus.

As the ultrasonic probe 2, a 1D array probe with a plurality of ultrasonic transducers arranged in a row in a specified direction (a scanning direction), or a 2D array probe with a plurality of ultrasonic transducers placed two-dimensionally is used. Otherwise, a 1D array probe in which ultrasonic transducers are arranged in a scanning direction and the ultrasonic transducers can be mechanically swung in a direction perpendicular to the scanning direction (a swinging direction) may be used.

The transmitter/receiver 3 includes a transmitter and a receiver. The transmitter/receiver 3 supplies an electric signal to the ultrasonic probe 2 to make it generate ultrasonic waves, and receives an echo signal received by the ultrasonic probe 2.

The transmitter of the transmitter/receiver 3 is provided with a clock-generating circuit, a transmission delay circuit, and a pulsar circuit, which are not illustrated. The clock-generating circuit generates a clock signal that determines the transmission timing or transmission frequency of ultrasonic signals. The transmission delay circuit delays ultrasonic waves at the time of transmission thereof to execute transmission focus. The pulsar circuit has the same number of pulsars as individual channels corresponding to the respective ultrasonic transducers, and generates a driving pulse at delayed transmission timing to supply an electrical signal to each of the ultrasonic transducers of the ultrasonic probe 2.

The receiver of the transmitter/receiver 3 is provided with a preamplifier circuit, an A/D conversion circuit, a reception delay circuit, and an adding circuit. The preamplifier circuit amplifies echo signals outputted from the respective ultrasonic transducers of the ultrasonic probe 2, for each reception channel. The A/D conversion circuit subjects the amplified echo signals to A/D conversion. The reception delay circuit gives a delay time necessary for determining the reception directionality to the echo signals after the A/D conversion. The adding circuit adds the delayed echo signals. By the addition, a reflection component from a direction corresponding to the reception directionality is intensified. Here, the signals subjected to the addition process by the transmitter/receiver 3 may be referred to as "RF data (raw data)." The transmitter/receiver 3 outputs the RF data to the signal processor 4.

The signal processor 4 is provided with a B-mode processor, a CFM processor, etc. The B-mode processor performs imaging of the amplitude information of echoes. To be specific, the B-mode processor executes Band Pass Filter processing on the reception signals outputted from the transmitter/receiver 3, and thereafter detects the envelope of the outputted signals. Then, the B-mode processor executes compression processing by logarithm conversion on the detected data, thereby performing imaging of the amplitude information of the echoes. Further, the CFM processor performs imaging of information on a moving blood flow. The blood-flow information is information such as a speed, dispersion and power. The blood-flow information is obtained as binary information.

The image generator 5 converts the data after the signal processing into data of a coordinate system based on spatial coordinates (digital scan conversion). For example, the image generator 5 executes scan-conversion processing on the data after the signal processing outputted from the B-mode processor, thereby generating B-mode image data (may be referred to as "tomographic image data" hereinafter) showing the tissue shape of a subject. The image generator 5 then outputs ultrasonic image data, such as the tomographic image data, to the storage 6.

Further, in a case where volume scan is performed by the ultrasonic probe 2 and the transmitter/receiver 3, the image generator 5 may receive volume data from the signal processor 4 and execute volume rendering on the volume data, thereby generating three-dimensional image data that sterically shows a tissue. Furthermore, the image generator 5 may execute MPR processing (Multi-Planar Reconstruction) on the volume data, thereby generating image data (MPR image data) at an arbitrary cross section. The image generator 5 then outputs ultrasonic image data, such as three-dimensional image data and MPR image data, to the storage 6.

The ultrasonic image data such as tomographic image data and three-dimensional image data generated by the image generator 5 is stored into the storage 6. Moreover, in a case where ECG (Electrocardiogram) signals of the subject have been acquired, the controller 9 receives the ECG signals from the outside of the ultrasonic imaging apparatus 1, and causes the storage 6 to store in a state where the ultrasonic image data is associated with a cardiac phase received at timing when the ultrasonic image data has been generated.

The ultrasonic imaging apparatus 1 according to the first embodiment scans the heart of a subject with ultrasonic waves to acquire tomographic image data showing the heart for each cardiac phase. That is, the ultrasonic imaging apparatus 1 acquires moving image data of the heart. For example, the ultrasonic imaging apparatus 1 acquires a plurality of tomographic image data (moving image data of a heart) during one cardiac cycle or more by scanning the heart of the subject with ultrasonic waves during one cardiac cycle or more. In a case where an ECG signal has been acquired, the controller 9 associates a cardiac phase received at timing when the tomographic image data has been generated with each of the tomographic image data, and causes the storage 6 to store. Consequently, a cardiac phase in which the tomographic image data has been generated is associated with each of the plurality of tomographic image data, and stored into the storage 6.

The display controller 7 retrieves tomographic image data from the storage 6 and causes a display 81 to display a tomographic image based on the tomographic image data. For example, when an operator designates an arbitrary time phase by using an operation part 82, information that indicates the designated time phase is outputted to the display controller 7 from the operation part 82. The display controller 7 retrieves, from the storage 6, tomographic image data to which the designated time phase is associated, and causes the display 81 to display a tomographic image based on the tomographic image data.

The image processor 10 includes a contour tracking part 11 and a marker generator 12. The image processor 10 sets a contour designated on a tomographic image showing a heart as an initial contour, and obtains the position of each of points composing the contour at each cardiac phase, by performing pattern matching of two tomographic images acquired at different cardiac phases.

Here, a method for designating the abovementioned initial contour will be described. In the present embodiment, a case of designating the endocardial contour and the epicardial contour of a heart as a specific tissue will be described. First, the operator designates an arbitrary cardiac phase by using the operation part 82. The display controller 7 retrieves, from the storage 6, tomographic image data acquired at the cardiac phase designated by the operator, and causes the display 81 to display a tomographic image based on the tomographic image data. In this embodiment, tomographic image data of a heart is acquired, so that the tomographic image of the heart is displayed in the display 81. For example, cross-sectional image data of a heart is acquired by transmitting/receiving ultrasonic waves, and a cross-sectional image of the heart is displayed in the display 81.

For example, when the end diastole (a cardiac phase at which an R wave has been detected) or the end systole (a cardiac phase after a lapse of a specified time from the cardiac phase at which an R wave has been detected) is designated by the operator, the display controller 7 retrieves, from the storage 6, tomographic image data acquired in the end diastole or tomographic image data acquired in the end systole, and causes the display 81 to display a tomographic image based on the tomographic image data.

Because a cardiac phase at which the tomographic image data has been acquired is stored in the storage 6 in association with the tomographic image data, the display controller 7 retrieves, from the storage 6, tomographic image data acquired at a cardiac phase such as the end diastole and the end systole, and causes the display 81 to display a tomographic image based on the tomographic image data at the cardiac phase.

In a tomographic image of the heart, not only the endocardium and epicardium of the heart, but also papillary muscles, chordae, etc. are shown. While observing the tomographic image of the heart displayed in the display 81 (for example, a cross-sectional image of the heart), the operator designates the endocardial contour of the heart by using the operation part 82 so as not to include the papillary muscles or chordae shown in the tomographic image of the heart. In evaluation of the myocardium, the endocardium is designated while avoiding the papillary muscles and chordae because the papillary muscles and chordae become noise. For example, the operator traces a two-dimensional contour of the endocardium shown in a tomographic image by using the operation part 82, thereby designating the two-dimensional contour of the endocardium. Thus, when the two-dimensional contour of the endocardium is designated, coordinate information of the two-dimensional contour of the endocardium is outputted to the image processor 10 from the user interface (UI) 8 via the controller 9.

Furthermore, the operator traces a two-dimensional contour of the epicardium shown in the tomographic image by using the operation part 82, thereby designating the two-dimensional contour of the epicardium. Thus, when the two-dimensional contour of the epicardium is designated, coordinate information of the two-dimensional contour of the epicardium is outputted to the image processor 10 from the user interface (UI) 8 via the controller 9.

In the image processor 10, the contour tracking part 11 receives the coordinate information of the endocardial contour and the coordinate information of the epicardial contour from the user interface (UI) 8. The two-dimensional contour of the endocardium designated here is set as an initial endocardial contour into the contour tracking part 11. Likewise, the designated two-dimensional contour of the epicardium is set as an initial epicardial contour into the contour tracking part 11. For example, the two-dimensional contours of the endocardium and the epicardium at a cardiac phase in which an R wave has been detected are set as the initial contours into the contour tracking part 11.

As described above, when the two-dimensional contour of the endocardium (initial endocardial contour) at any cardiac phase is designated by the operator, the contour tracking part 11 performs pattern matching using speckle patterns for two tomographic image data acquired at different times.

The contour tracking part 11 obtains the position of each of points composing the two-dimensional contour of the endocardium designated by an initial contour for each tomographic image data acquired at each cardiac phase through pattern matching. Then, the contour tracking part 11 temporally tracks each of the points composing the two-dimensional contour of the endocardium.

For example, the contour tracking part 11 receives coordinate information of each of the points composing the endocardial contour designated as the initial contour, and further retrieves, from the storage 6, tomographic image data (may be referred to as "tomographic image data B" hereinafter) generated at a cardiac phase following the tomographic image data (may be referred to as "tomographic image data B" hereinafter) at which the initial contour has been detected. The contour tracking part 11 then performs pattern matching using speckle pattern for two tomographic image data that are temporally sequential to obtain the shift vector of each of points composing the endocardial contour designated as the initial contour. That is, the contour tracking part 11 obtains the shift vector of each point on the endocardial contour through pattern matching. To be specific, the contour tracking part 11 obtains the shift vector of each of points composing the endocardial contour by performing pattern matching for the tomographic image data A and the tomographic image data B by using speckle patterns.

This shift vector represents the displacement of each of points composing the contour and the shifted direction to which each point has been displaced. That is, the contour tracking part 11 performs pattern matching for two tomographic image data acquired at different times and calculates the shifted amount of the speckles to obtain the shift vector of each of points composing the contour. Obtaining the shift vector of each of points composing the contour makes it possible to obtain the position of each of points composing the endocardial contour in the cardiac phase during which the tomographic image data B has been generated.

Furthermore, the contour tracking part 11 retrieves, from the storage 6, tomographic image data generated at a cardiac phase following the tomographic image data B (may be referred to as "tomographic image data C" hereinafter). Then, the contour tracking part 11 performs pattern matching using speckle patterns for the temporally sequential two tomographic image data (tomographic image data B and tomographic image data C) to obtain the shift vector of each of the points composing the endocardial contour.

Consequently, the position of each of the points composing the endocardial contour at the cardiac phase at which the tomographic image data C has been generated is obtained.

As described above, the contour tracking part 11 obtains the shift vector at each of the points composing the endocardial contour set as the initial contour, by pattern matching using speckle patterns, for each cardiac phase at which each tomographic image data has been generated. Consequently, the contour tracking part 11 temporally tracks the shift vector at each of the points composing the endocardial contour. As a result, it becomes possible to temporally track each of the points composing the two-dimensional contour of the endocardium. For example, the contour tracking part 11 obtains the position of each of the points composing the two-dimensional contour of the endocardium at each cardiac phase, with respect to all the tomographic image data acquired during one cardiac cycle. Consequently, the position of each of the points composing the two-dimensional contour of the endocardium at each cardiac phase is obtained throughout one cardiac cycle.

When the two-dimensional contour of the epicardium (the initial contour of the epicardium) is set, the contour tracking part 11 performs pattern matching using speckle patterns for two tomographic image data acquired at different times, as in the tracking of the endocardium. Through this pattern matching, the contour tracking part 11 obtains the position of each of the points composing the two-dimensional contour of the epicardium, for each tomographic image data generated at each cardiac phase. Then, the contour tracking part 11 temporally tracks each of the points composing the two-dimensional contour of the epicardium.

The contour tracking part 11 may obtain the normal vector at each of points composing a designated endocardium and define a position that is a fixed distance outside the endocardium in the normal vector direction as the two-dimensional contour of the epicardium of a heart. For example, the contour tracking part 11 defines a position that is 8 mm outside the position of the endocardium as the epicardial contour. This fixed distance can be changed to any value by the operator. The two-dimensional contour of the epicardium defined here is set as the initial contour of the epicardium to become a tracking target in the contour tracking part 11. Then, the contour tracking part 11 temporally tracks each of the points composing the two-dimensional contour of the epicardium.

Then, the contour tracking part 11 outputs coordinate information of each of the points composing the two-dimensional contour of the endocardium at each cardiac phase and coordinate information of each of the points composing the two-dimensional contour of the epicardium to the computing part 20. The computing part 20 is provided with a wall-motion-information calculator 21, a differential-value calculator 22, a normalizing part 23, and a color determining part 24. The computing part 20 receives the coordinate information of each of the points composing the two-dimensional contours of the endocardium and the epicardium at each cardiac phase from the contour tracking part 11, and obtains wall-motion information of a heart. Hereinafter, the function of each of the parts composing the computing part 20 will be described.

The wall-motion-information calculator 21 obtains wall-motion information of a heart based on the coordinate information of each of the points composing the two-dimensional contour of the endocardium at each cardiac phase and the coordinate information of each of the points composing the two-dimensional contour of the epicardium at each cardiac phase. For example, the wall-motion-information calculator 21 obtains wall-motion information, such as strain, rotation, twist and torsion of the myocardium.

As one example, a case of obtaining the strain of a myocardium will be described. The wall-motion-information calculator 21 obtains displacement of the endocardium at each cardiac phase, based on the coordinate information of each of the points composing the two-dimensional contour of the endocardium at each cardiac phase. Further, the wall-motion-information calculator 21 obtains displacement of the epicardium at each cardiac phase, based on the coordinate information of each of the points composing the two-dimensional contour of the epicardium at each cardiac phase. The wall-motion-information calculator (strain calculator) 21 then obtains strain of the myocardium at each cardiac phase, based on the displacement of the endocardium and the displacement of the epicardium at each cardiac phase. For example, the wall-motion-information calculator 21 regards a cardiac phase in which an R wave has been detected as an initial time phase, and compares the two-dimensional contour of the endocardium at the initial time phase with the two-dimensional contour of the endocardium at another cardiac phase to obtain the displacement of the endocardium at each cardiac phase. Further, the wall-motion-information calculator 21 compares the two-dimensional contour of the epicardium at the initial time phase with the two-dimensional contour of the epicardium at another cardiac phase to obtain the displacement of the epicardium at each cardiac phase. The wall-motion-information calculator 21 then obtains strain at each cardiac phase, based on the displacement at each cardiac phase.

As one example, a case of obtaining the strain in a wall-thickness direction will be described. The strain in the wall-thickness direction is defined as strain in the thickness direction between the endocardium and the epicardium. As described above, in a case where the two-dimensional contour of the endocardium and the two-dimensional contour of the epicardium are obtained at each cardiac phase, the wall-motion-information calculator 21 obtains the strain in the wall-thickness direction at each cardiac phase, based on the coordinate information of each of the points composing the two-dimensional contour of the endocardium at each cardiac phase and the coordinate information of each of the points composing the two-dimensional contour of the epicardium at each cardiac phase.

Figure 2:
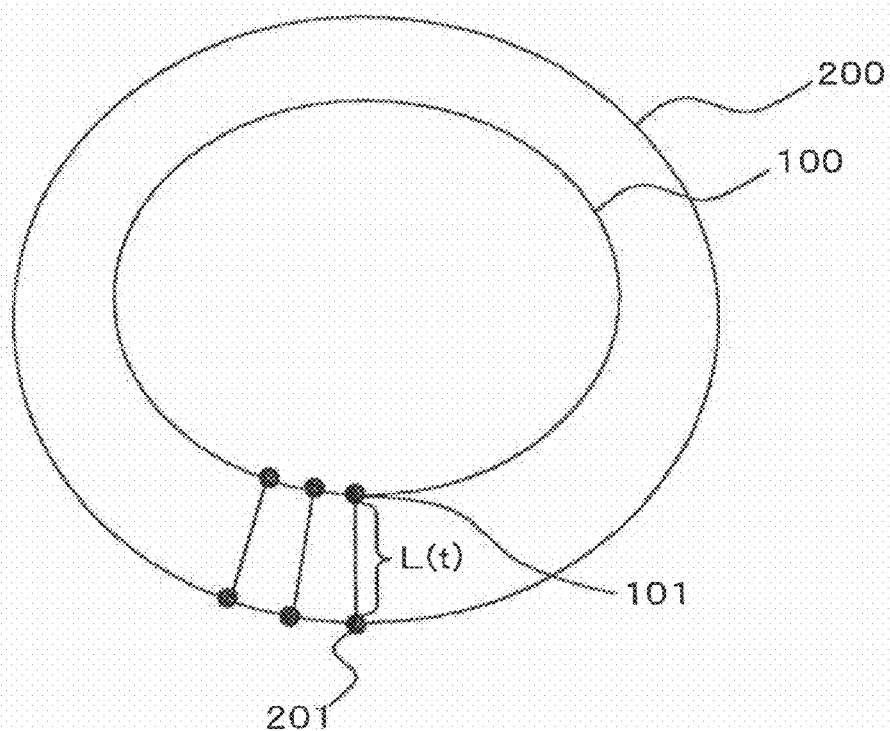
FIG. 2 is a view schematically showing an endocardial contour and an epicardial contour.

A process for obtaining the strain in the wall-thickness direction will be described with reference to FIG. 2. FIG. 2 is a view schematically showing the endocardial contour and the epicardial contour.

For example, the wall-motion-information calculator 21 obtains a line orthogonal to a contour 100 of the endocardium at a point 101 on the contour 100 of the endocardium obtained by the contour tracking part 11. The wall-motion-information calculator 21 then obtains a point 201 where the orthogonal line crosses a contour 200 of the epicardium. The wall-motion-information calculator 21 obtains the strain between the point 101 and the point 201 (the strain in the wall-thickness direction) at each cardiac phase, based on a distance L (t)

between the point 101 on the contour 100 of the endocardium and the point 201 on the contour 200 of the epicardium at each cardiac phase.

For example, a cardiac phase at which the initial endocardial contour and the initial epicardial contour are set is regarded as an initial time phase, and a distance between the point 101 and the point 201 at the initial time phase is a distance $L(0)$. To be specific, in a case where the initial endocardial contour and the initial epicardial contour are designated on a tomographic image at a cardiac phase in which an R wave has been detected, the cardiac phase in which the R wave has been detected becomes the initial time phase. Further, the distance between the point 101 and the point 201 at any cardiac phase is set as the distance $L(t)$.

Then, the wall-motion-information calculator 21 receives the coordinate information of each of the points composing the two-dimensional contours of the endocardium and the epicardium at each cardiac phase, and obtains a difference $\Delta L(t)$ between the distance $L(t)$ at any cardiac phase and the distance $L(0)$ at the initial time phase. That is, the wall-motion-information calculator 21 calculates $L(t)-L(0)=\Delta L(t)$. The difference $\Delta L(t)$ is equivalent to the displacement of the membrane thickness.

Next, the wall-motion-information calculator 21 obtains strain $S(t)$ in the wall-thickness direction at any cardiac phase by dividing the difference $\Delta L(t)$ by the distance $L(0)$ at the initial time phase. That is, the wall-motion-information calculator (strain calculator) 21 calculates $\Delta L(t)/L(0)=S(t)$.

The wall-motion-information calculator 21 obtains the strain $S(t)$ in the wall-thickness direction at every specified interval on the contour 100 of the endocardium and the contour 200 of the epicardium. That is, the wall-motion-information calculator 21 obtains the strain $S(t)$ at a plurality of locations in the endocardium and the epicardium of a heart. For example, the wall-motion-information calculator 21 obtains the strain $S(t)$ at 360 locations in total by obtaining the strain $S(t)$ in the wall-thickness direction at every interval of 1° on the contours 100 and 200.

Thus, the wall-motion-information calculator 21 obtains, for each cardiac phase, the strain $S(t)$ in the wall-thickness direction in each location of the myocardium. Then, the wall-motion-information calculator 21 outputs the strain $S(t)$ in the wall-thickness direction of each location at each cardiac phase to the differential-value calculator 22.

Furthermore, at an arbitrary cardiac phase, the all-motion-information calculator 21 obtains a maximum value of an absolute value of wall-motion information in each location of the myocardium, and outputs the maximum value to the normalizing part 23. For example, in the case of evaluating a heart during one cardiac cycle, the wall-motion-information calculator 21 obtains the maximum value of the absolute value of the wall-motion information in each location of the myocardium during the one cardiac cycle.

As one example, the wall-motion-information calculator 21 obtains the maximum value (maximum strain Smax) of the absolute value of the strain in each location of the myocardium at any cardiac phase. The wall-motion-information calculator 21 then outputs the maximum strain Smax in each location of the myocardium to the normalizing part 23. For example, in the case of evaluating the heart during one cardiac cycle, the wall-motion-information calculator (strain calculator) 21 obtains the maximum strain Smax in each location of the myocardium during the one cardiac cycle.

The differential-value calculator 22 obtains a differential value indicating the temporal change rate of wall-motion information at each cardiac phase, by executing time-differentiation of the wall-motion information of each location at each cardiac phase. Then, the differential-value calculator 22 outputs the differential value of each location at each cardiac phase to the normalizing part 23. As one example, the differential-value calculator 22 obtains a strain rate (speed) $SR(t)$ indicating the temporal change rate of the strain $S(t)$, by executing time-differentiation of the strain $S(t)$ in the wall-thickness direction of each location at each cardiac phase. Then, the differential-value calculator 22 outputs the strain rate $SR(t)$ of each location at each cardiac phase to the normalizing part 23.

The normalizing part 23 obtains a normalized differential value by dividing the differential value of each location at each cardiac phase by the maximum value of the wall-motion information in each location. Then, the normalizing part 23 outputs the normalized differential value to the color determining part 23. As one example, the normalizing part 23 normalizes the maximum strain Smax by dividing the strain rate $SR(t)$ of each location at each cardiac phase by the maximum strain Smax of each location. That is, the normalizing part 23 calculates $SR(t)/Smax=nSR(t)$. The normalizing part 23 then outputs $nSR(t)$ of each location at each cardiac phase to the color determining part 24.

The color determining part 24 determines a color corresponding to the magnitude of the differential value normalized by the maximum value of the wall-motion information. For example, the color determining part 24 assigns different colors corresponding to the magnitudes of the normalized differential values. The colors to be assigned to the magnitudes of the respective normalized differential values are predetermined, and a table in which the magnitudes of the normalized differential values are associated with the colors is previously created and stored in a storage (not illustrated).

The color determining part 24 determines a color corresponding to the normalized differential value with reference to the table. Then, the color determining part 24 outputs, to the display controller 7, coordinate information of each location at each cardiac phase and information indicating the color assigned to the location.

As one example, the color determining part 24 determines a color corresponding to the magnitude of the strain rate $nSR(t)$ normalized by the maximum strain Smax. For example, the color determining part 24 assigns different colors in accordance with the magnitudes of the normalized strain rates $nSR(t)$. The colors to be assigned to the magnitudes of the respective strain rates $nSR(t)$ are predetermined. A table in which the magnitudes of the strain rates $nSR(t)$ are associated with the colors is previously created and stored in a storage (not illustrated). In this table, different colors depending on the magnitudes of the strain rates $nSR(t)$ are associated in the table. The color determining part 24 determines the color corresponding to the magnitude of the strain rate $nSR(t)$ of each location at each cardiac phase.

The color determining part 24 outputs, to the display controller 7, coordinate information of each location at each cardiac phase and information indicating the color assigned to the location.

The display controller 7 controls the display 81 so as to display a tomographic image based on the tomographic image data acquired at each cardiac phase. Furthermore, the display controller 7 receives, from the color determining part 24, coordinate information of each location of the myocardium (a range between the endocardium) and the epicardium) at each cardiac phase and information indicating the color assigned to each location.

The display controller 7 controls the display 81 to display in the color predetermined by the color determining part 24 and determined to each location of the myocardium on the tomographic image of each cardiac phase.

At this moment, the display controller 7 controls the display 81 to display in the color determined and assigned to each location, within a range having a specified width with each location being the center thereof.

Figure 3:
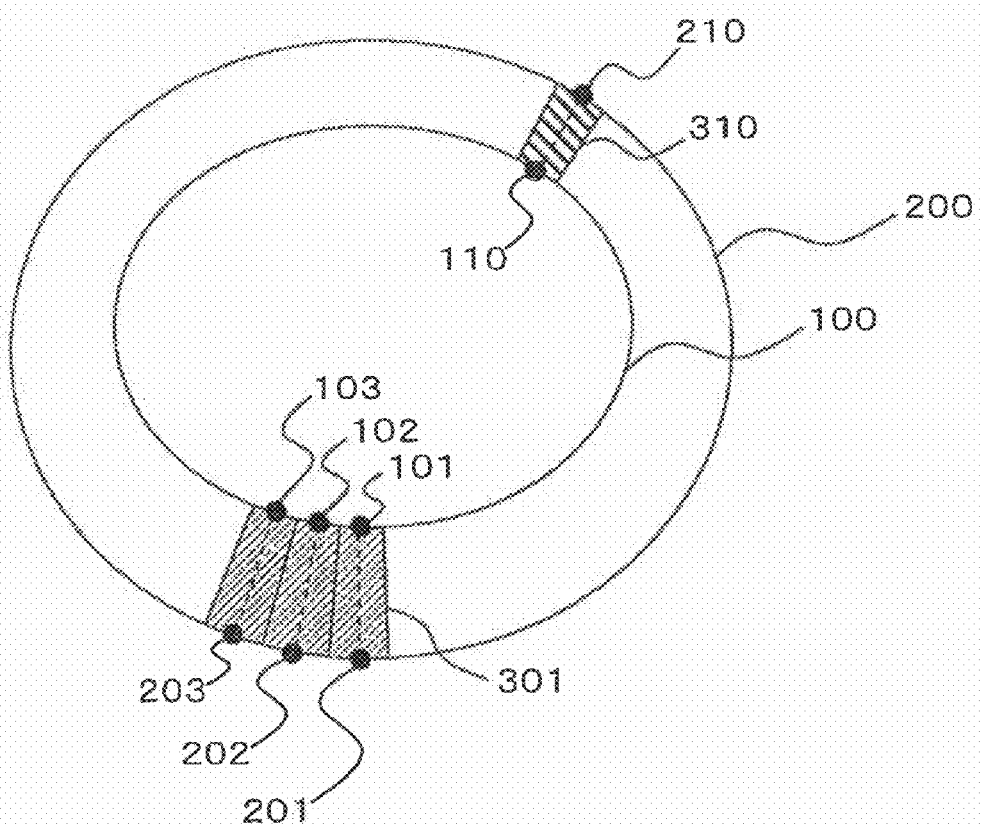
FIG. 3 is a view schematically showing an endocardial contour and an epicardial contour.

Here, one example of coloring to each location will be described with reference to FIG. 3. FIG. 3 is a view schematically showing the endocardial contour and the epicardial contour. When receiving the coordinate information of each location of the myocardium (the range between the endocardium and the epicardium) at each cardiac phase and information indicating a color assigned to each location from the color determining part 24, the display controller 7 controls the display 81 to display in the colors determined and assigned to each location in the range between the contour 100 of the endocardium and the contour 200 of the epicardium shown in the tomographic image.

For example, the display controller 7 controls the display 81 to display in the color determined and assigned to a range 301 that is between the point 101 on the contour 100 of the endocardium and the point 201 on the contour 200 of the epicardium and that has a specified width in a circumferential direction. In a case where the normalized strain rate nSR(t) is obtained at every interval of 1°, the display controller 7 assigns colors corresponding to the magnitudes of the normalized strain rates nSR(t) and controls the display 81 to display the colors, for every interval of 1°. For example, the display controller 7 controls the display 81 to display in a color determined and assigned to a range that is between the point 102 on the contour 100 of the endocardium and the point 202 on the contour 200 of the epicardium and that has a specified width in the circumferential direction.

Likewise, the display controller 7 controls the display 81 to display in a color determined and assigned to a range between the point 103 on the contour 100 of the endocardium and the point 203 on the contour 200 of the epicardium.

Because different colors are assigned depending on the magnitudes of the normalized strain rates nSR(t) and displayed in the display 81, it is possible to easily recognize the magnitudes of the strain rates nSR(t) at the respective locations of the myocardium by referring to the colors. Then, by observing the colors displayed in the display 81, it is possible to evaluate the diastolic function of a heart. That is, in a case where the color assigned to a certain location is different from the colors assigned to the other locations, it is possible to easily grasp the abnormality of the diastolic function in the location. For example, in a case where a different color from those of the other locations is assigned to the range 310 between the point 110 on the endocardial contour 100 and the point 210 on the epicardial contour 200, it becomes possible to easily grasp that the diastolic function in the location corresponding to the range 310 is abnormal. To be specific, it becomes possible to easily grasp the deterioration or enhancement of the diastolic function in the location.

Further, the marker generator 12 generates a marker indicating the initial contour of the endocardium, based on coordinate information of the two-dimensional contour of the endocardium designated by the operator. Likewise, the marker generator 12 generates a marker indicating the initial contour of the epicardium, based on coordinate information of the two-dimensional contour of the epicardium designated by the operator. The display controller 7 controls the display 81 to display a tomographic image based on tomographic image data with the initial contours designated, and furthermore controls the display 81 to display the markers indicating the initial contours in the superimposed state on the tomographic image.

Moreover, when receiving, from the contour tracking part 11, the coordinate information of each of the points composing the two-dimensional contour of the endocardium at each cardiac phase, the marker generator 12 generates a marker indicating the two-dimensional contour of the endocardium at each cardiac phase. Further, when receiving, from the contour tracking part 11, the coordinate information of each of the points composing the two-dimensional contour of the epicardium at each cardiac phase, the marker generator 12 generates a marker indicating the two-dimensional contour of the epicardium at each cardiac phase. The display controller 7 controls the display 81 to sequentially display, for each cardiac phase, a tomographic image based on the tomographic image data acquired at each cardiac phase. Besides, the display controller 7 controls the display 81 to sequentially display the markers indicating the contours of the endocardium and the epicardium at each cardiac phase in the superimposed state on the tomographic image acquired at each cardiac phase. The display controller 7 controls the display 81 to sequentially update and display the tomographic images and the markers in the display 81.

Figure 4:
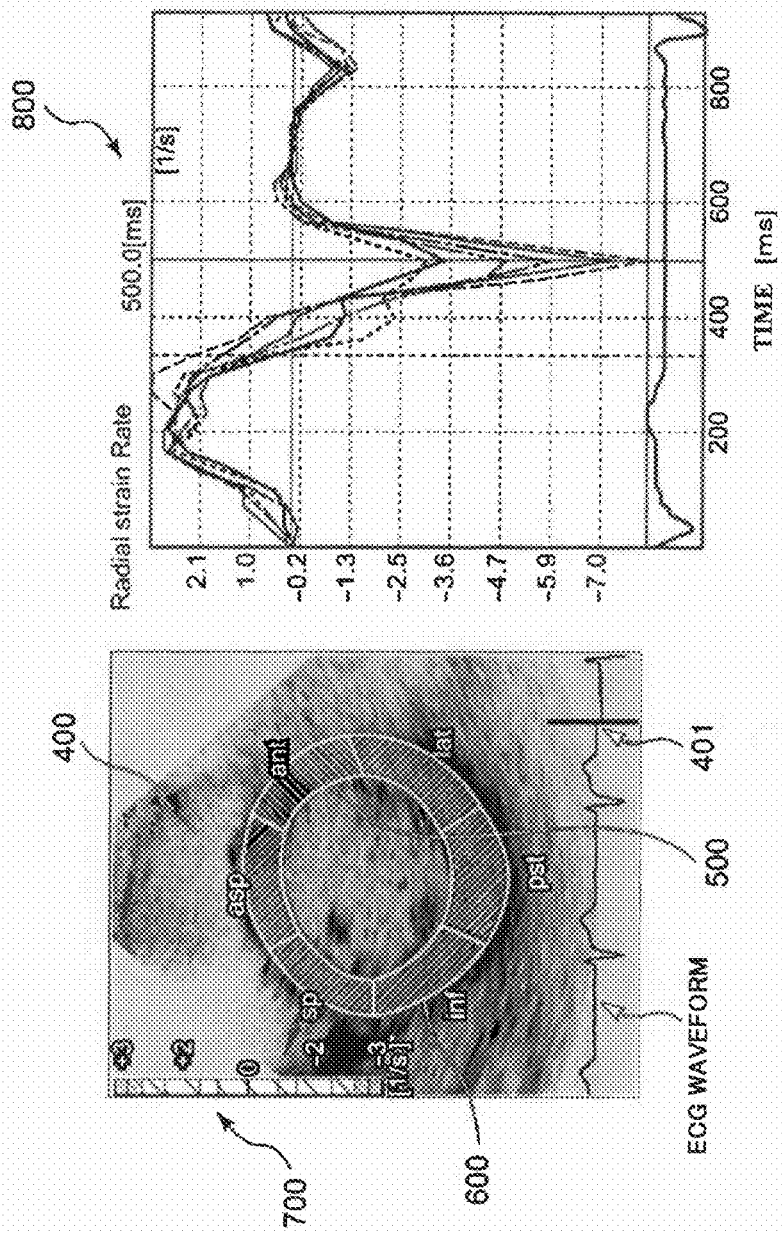
FIG. 4 is a view showing an image acquired by the ultrasonic imaging apparatus according to the embodiment of the present invention, and motion information.

An example of the contours of the endocardium and epicardium, the motion information and the tomographic images obtained in the above manner is shown in FIG. 4. FIG. 4 is a view showing an image and wall-motion information acquired by the ultrasonic imaging apparatus according to the embodiment of the present invention.

The display controller 7 retrieves tomographic image data from the storage 6 and controls the display 81 to display a tomographic image 400 based on the tomographic image data. In the example shown in FIG. 4, the tomographic image 400 represents a minor-axis image of a heart. The display controller 7 controls the display 81 to display a marker 500 indicating the endocardial contour corresponding to a cardiac phase at which the tomographic image data has been acquired in the superimposed state on the tomographic image 400. Furthermore, the display controller 7 controls the display 81 to display a marker 600 indicating the epicardial contour corresponding to the cardiac phase at which the tomographic image data has been acquired in the superimposed state on the tomographic image 400 together with the marker 500. The display controller 7 sequentially updates and controls the display 81 to display, for each cardiac phase, the tomographic image 400 acquired at each cardiac phase, the marker 500 indicating the endocardial contour, and the marker 600 indicating the epicardial contour.

Furthermore, the display controller 7 controls the display 81 to display wall-motion information at each cardiac phase obtained by the computing part 20, for each cardiac phase. For example, as shown in FIG. 4, the display controller 7 assigns colors corresponding to the magnitudes of the normalized strain rates nSR(t) of the respective locations to ranges of the respective locations between the maker 500 of the endocardium and the marker 600 of the epicardium, and controls the display 81 to display the colors in the superimposed state on the tomographic image 400.

The display controller 7 sequentially updates and controls the display 81 to display the tomographic image 400 acquired at each cardiac phase, the marker 500 indicating the endocardial contour, the marker 600 indicating the epicardial contour, and the wall-motion information. Further, the display controller 7 controls the display 81 to display a color bar 700 in which the magnitudes of the normalized strain rates nSR(t)

are associated with the colors. The operator can evaluate the cardiac function in each location of a heart by referring to the color bar 700.

Because different colors are assigned corresponding to the magnitudes of the normalized strain rates and are displayed in the display 81, it becomes possible to easily grasp the deterioration or enhancement of the diastolic function in each location by observing the color.

Further, as shown in FIG. 4, the computing part 20 may set the position of the center of gravity in a minor-axis image of a heart and radially draw straight lines from the position of the center of gravity to divide the minor-axis image into six regions as recommended by the ASE (American Society of Echocardiography). In this case, the computing part 20 obtains the strains or strain rates at a plurality of locations included in each of the regions and obtains the average value of the strains or the average value of the strain rates at the plurality of locations to obtain the average value of the strains or the average value of the strain rates in each of the regions. In the example shown in FIG. 4, the computing part 20 divides the tomographic image 400 equivalent to the minor-axis image into six regions: int (inferior wall) D1, pst (posterior wall) D2, lat (lateral wall) D3, ant (anterior wall) D4, asp (anterior-septum) D5, and sp (septum) D6. Then, the computing part 20 obtains the average value of the strains or the average value of the strain rates in the wall-thickness direction (a direction of thickness between the endocardium and the epicardium) for each of the regions D1-D6.

Further, the computing part 20 may graph temporal changes of the average value of the normalized strain rates nSR(t) in each of the regions. The display controller 7 receives graph data showing the temporal changes of the average value of the strains from the computing part 20, and controls the display 81 to display a graph. For example, as shown in FIG. 4, the display controller 7 controls the display 81 to display a graph 800 generated by the computing part 20 to show the temporal changes of the average value of the strains in each of the regions. In the graph 800 in FIG. 4, time [ms] is taken on the horizontal axis, and the strain rate in the circumferential direction (Radial Strain Rate) is taken on the vertical axis.

Moreover, the display controller 7 may control the display 81 to display an ECG waveform and control the display 81 to display a bar 401 indicating the cardiac phase at which the tomographic image displayed in the display 81 has been acquired, in the superimposed state on the ECG waveform. Then, the display controller 7 moves the bar 401 on the ECG waveform and controls the display 81 to display the tomographic image 400, the marker 500 and the marker 600 at the cardiac phase indicated by the bar 401. Furthermore, the display controller 7 controls the display 81 to display colors assigned corresponding to the magnitudes of the strain rates nSR(t) of the respective locations at the cardiac phase indicated by the bar 401.

The user interface (UI) 8 is provided with the display 81 and the operation part 82. The display 81 is composed of a monitor such as a CRT and a liquid crystal display, and displays a tomographic image, a three-dimensional image, etc. on its screen. The operation part 82 is composed of a keyboard, a mouse, a trackball, or a TCS (Touch Command Screen), and is operated by the operator to give various kinds of instructions.

The controller 9 is connected to each part of the ultrasonic imaging apparatus 1 to control the operation of each part.

Furthermore, the image processor 10 is provided with a CPU (Central Processing Unit) and a storage such as a ROM (Read-Only Memory), a RAM (Random Access Memory) and an HDD (Hard Disk Drive) (not illustrated). The storage stores image-processing programs for executing the functions of the respective parts of the image processor 10. The image-processing programs include a contour-tracking program for executing the function of the contour tracking part 11, and a marker-generating program for executing the function of the marker generator 12. When the CPU executes the contour-tracking program, the endocardial contour and the epicardial contour at each cardiac phase are obtained. Moreover, when the CPU executes the marker-generating program, the marker indicating the endocardial contour and the marker indicating the epicardial contour are generated.

Furthermore, the computing part 20 is provided with a CPU and a storage such as a ROM, a RAM and an HDD (not illustrated). The storage stores a computing program for executing the function of the computing part 20. The computing program includes: a wall-motion-information calculating program for executing the function of the wall-motion-information calculator 21; a differential-value calculating program for executing the function of the differential-value calculator 22; a normalization program for executing the function of the normalizing part 23; and a color-determining program for executing the function of the color determining part 24. When the CPU executes the wall-motion-information calculating program, the wall-motion information of each location at each cardiac phase is obtained. Further, when the CPU executes the differential-value calculating program, the differential value of the wall-motion information of each location at each cardiac phase is obtained. Moreover, when the CPU executes the normalization program, the differential value of each location at each cardiac phase is divided by the maximum value of the wall-motion information of each location, and as a result, a normalized differential value is obtained. In addition, when the CPU executes the color-determining program, a color corresponding to the magnitude of the normalized differential value is determined.

Moreover, the display controller 7 is provided with a CPU and a storage such as a ROM, a RAM and an HDD (not illustrated). The storage stores a display control program for executing the function of the display controller 7. Then, when the CPU executes the display control program, a tomographic image, a marker and wall-motion information are displayed in the display 81.

Thus, by normalizing the differential value of the wall-motion information of each location by the maximum value of the absolute value of the wall-motion information, it becomes possible to reduce the influence of variations in wall-motion information on the differential value of the wall-motion information. Consequently, it becomes possible to more appropriately perform diastolic function evaluation using the differential value of the wall-motion information. For example, by normalizing the strain rate of each location by the maximum value of the absolute value of the strain, it becomes possible to reduce the influence of variations in strain on the strain rate. Consequently, it becomes possible to more appropriately perform diastolic function evaluation using the strain rate.

In conventional techniques, a strain rate (a differential value of wall-motion information) that is not normalized is used. Therefore, when there are variations in the strains (wall-motion information), the strain rate is influenced by the variations. Consequently, colors assigned to the respective locations also vary, so that it has been difficult to accurately evaluate the diastolic function. On the contrary, the ultrasonic imaging apparatus 1 according to the present embodiment assigns colors corresponding to the magnitudes of the normalized strain rates to the respective locations and display the colors. Therefore, even if there are variations in strain, it is possible to reduce the variations. Consequently, it is possible to display while reducing variations in colors assigned to the respective locations, and therefore, it becomes possible to appropriately evaluate the diastolic function.

Furthermore, by assigning colors corresponding to the magnitudes of the normalized strain rates to the respective locations and controlling the display 81 to display the colors, it becomes possible to grasp the difference in color at each of the locations and easily evaluate the diastolic function at each of the locations. To be specific, because it is possible to easily grasp the strain rates at the respective locations based on the difference in colors at the respective locations, it becomes possible to easily grasp the deterioration or enhancement of the diastolic functions at the respective locations.

(Ultrasonic Image Processing Apparatus)

Further, an ultrasonic image processing apparatus configured to obtain wall-motion information by tracking the endocardial contour and the epicardial contour may be disposed outside the ultrasonic diagnostic apparatus. The ultrasonic image processing apparatus comprises the storage 6, the display controller 7, the user interface 8, the image processor 10, and the computing part 20, which are described above. The ultrasonic image processing apparatus acquires a plurality of tomographic image data, which have been serially acquired in time sequence, from the ultrasonic diagnostic apparatus disposed outside, and obtains wall-motion information by tracking the endocardial contour and the epicardial contour based on the plurality of tomographic image data.

By scanning a heart with ultrasonic waves by the ultrasonic diagnostic apparatus disposed outside the ultrasonic image processing apparatus, tomographic image data is acquired for each cardiac phase. The ultrasonic image processing apparatus receives the plurality of the tomographic image data acquired by the ultrasonic diagnostic apparatus and causes the storage 6 to store the plurality of tomographic image data. The image processor 10 of the ultrasonic image processing apparatus tracks the contours of the endocardium and epicardium by obtaining the position of each of the points composing the two-dimensional contours of the endocardium and the epicardium at each cardiac phase. Then, the computing part 20 of the ultrasonic image processing apparatus obtains the differential value of wall-motion information based on the position of each of the points composing the two-dimensional contours of the endocardium and the epicardium tracked by the image processor 10, and further obtains the normalized differential value. Furthermore, the computing part 20 determines colors corresponding to the magnitudes of the normalized differential values.

Thus, in a similar manner as the aforementioned ultrasonic imaging apparatus 1, the ultrasonic image processing apparatus disposed outside the ultrasonic imaging apparatus makes it possible to reduce the influence of variations in wall-motion information on the differential value by normalizing the differential value of the wall-motion information in each location by the maximum value of the absolute value of the wall-motion information. Consequently, it is possible to more appropriately evaluate the diastolic function using the differential value of wall-motion information.

(Operation)

Figure 5:
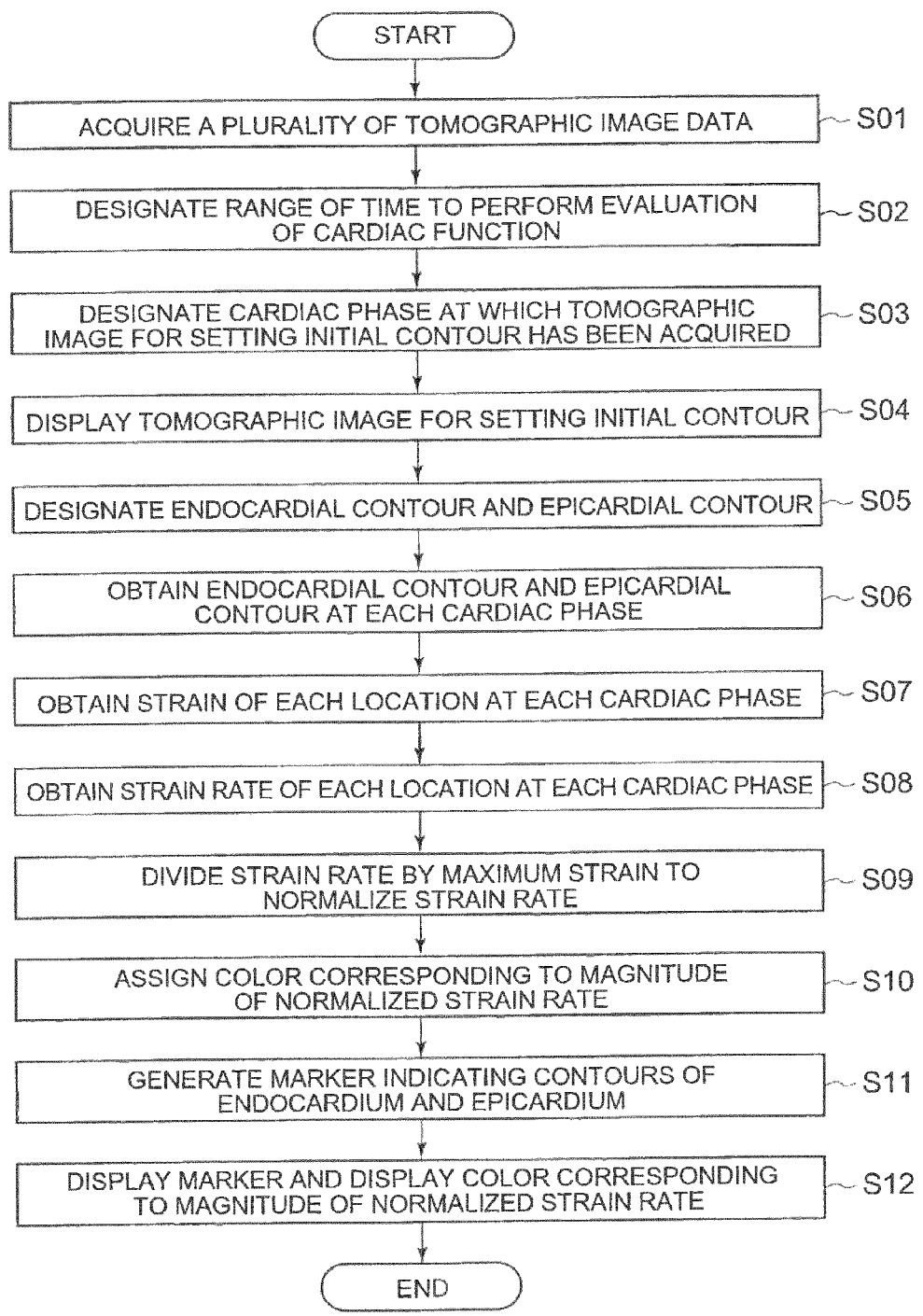
FIG. 5 is a flow chart showing a series of operations performed by the ultrasonic imaging apparatus according to the embodiment of the present invention.

Next, the operation of the ultrasonic imaging apparatus according to the embodiment of the present invention will be described with reference to FIG. 5. FIG. 5 is a flow chart for explaining a series of operations performed by the ultrasonic imaging apparatus according to the embodiment of the present invention. In this embodiment, a heart is a diagnosed location, and a plurality of tomographic image data (moving image data), which have been serially acquired in time sequence, are acquired. Then, based on the tomographic image data, the two-dimensional contours of the endocardium and epicardium of the heart are tracked, which are used for evaluation of the heart function.

(Step S01)

Firstly, the ultrasonic probe 2 is applied to a subject and ultrasonic waves are transmitted to the heart of the subject, whereby the image generator 5 generates tomographic image data (moving image data of the heart) of each cardiac phase. For example, by transmitting and receiving ultrasonic waves during one cardiac cycle or more, tomographic image data of each cardiac phase is generated during the one cardiac cycle or more. The controller 9 receives an ECG signal from outside the ultrasonic imaging apparatus 1, and causes the storage 6 to store each of the generated tomographic image data in the associated state with the time phase at which the tomographic image data has been generated.

(Step S02)

Next, the operator designates a range of time to perform the evaluation of the cardiac function, by using the operation part 82. For example, the operator designates the systole or the diastole of the heart.

(Step S03)

Next, the operator designates the cardiac phase at which a tomographic image for setting an initial contour has been acquired, by using the operation part 82. For example, the operator designates the end diastole or the end systole.

(Step S04)

When the cardiac phase is designated by the operator, the display controller 7 retrieves tomographic image data associated with the cardiac phase from the storage 6, and controls the display 81 to display a tomographic image based on the tomographic image data. For example, in a case where a cardiac phase of a cardiac end diastole is designated, the display controller 7 retrieves tomographic image data associated with the cardiac phase of the end diastole from the storage 6, and controls the display 81 to display a tomographic image of the end diastole.

(Step S05)

For example, in a state where the tomographic image of the end diastole is displayed in the display 81, the operator designates the endocardial contour so as not to include the papillary muscles or chorda tendinea shown in the tomographic image, by using the operation part 82. When the endocardial contour is designated by the operator, the marker generator 12 generates a marker indicating the endocardial contour. The display controller 7 controls the display 81 to display the maker indicating the endocardial contour in the superimposed state on the tomographic image of the end diastole. In addition, the operator designates the epicardial contour by using the operation part 82. When the epicardial contour is designated by the operator, the marker generator 12 generates a marker indicating the epicardial contour. The display controller 7 controls the display 81 to display the marker indicating the epicardial contour in the superimposed state on the tomographic image of the end diastole. The endocardial contour and epicardial contour designated here are set as initial contours in the contour tracking part 11.

(Step S06)

The contour tracking part 11 retrieves, from the storage 6, tomographic image data acquired at a cardiac phase following the tomographic image data in which the initial contours have been set, and conducts pattern matching using speckle patterns for the tomographic image data acquired at different times. Through this pattern matching, the contour tracking part 11 obtains the position of each of points composing a 2-dimensional endocardial contour and the position of each of points composing a 2-dimensional epicardial contour at the cardiac phase. Then, the contour tracking part 11 obtains the position of each of the points composing the endocardial and epicardial contours at each cardiac phase for the tomographic image data included in an analysis time range. For example, in a case where the systole of the heart is designated in Step S02, the contour tracking part 11 obtains the position of each of the points composing the endocardial and epicardial contours at each cardiac phase for the tomographic image data included in the systole.

(Step S07)

The wall-motion-information calculator 21 obtains a strain $S(t)$ in the wall-thickness direction in each location of the myocardium for each cardiac phase, as an example. In addition, the wall-motion-information calculator 21 obtains a maximum strain Smax in the analysis time range, in each location. At this moment, the wall-motion-information calculator 21 obtains the maximum value of the absolute values of strains in each location and regards the maximum value as the maximum strain Smax. For example, in a case where the systole of the heart is designated in Step S02, the wall-motion-information calculator 21 obtains the maximum strain Smax in the systole.

(Step S08)

The differential-value calculator 22 obtains a strain rate $SR(t)$ in each location for each cardiac phase, by temporarily differentiating the strain $S(t)$ in each location.

(Step S09)

The normalizing part 23 obtains a normalized strain rate $nSR(t)$ for each cardiac phase, by dividing the strain rate $SR(t)$ in each location by the maximum strain Smax in each location.

(Step S10)

The color determining part 24 assigns a color corresponding to the magnitude of the normalized strain rate $nSR(t)$ to each of the locations.

(Step S11)

The marker generator 12 receives coordinate information on each of the points composing the 2-dimensional endocardial contour at each cardiac phase, and generates a marker indicating the endocardial contour for each cardiac phase. Similarly, the marker generator 12 receives coordinate information on each of the points composing the 2-dimensional epicardial contour at each cardiac phase, and generates a marker that indicates the epicardial contour for each cardiac phase.

(Step S12)

The display controller 7 controls the display 81 to display a tomographic image based on the tomographic image data acquired at each cardiac phase. Moreover, the display controller 7 controls the display 81 to display the markers of the endocardium and epicardium at each cardiac phase in the superimposed state on the tomographic image at each cardiac phase. In addition, the display controller 7 controls the display 81 to display in the colors determined for each location by the color determining part 24 and assigned to each location on the tomographic image. The display controller 7 then sequentially updates the tomographic image acquired at each cardiac phase, the marker that indicates the endocardial contour, and the marker that indicates the epicardial contour for each cardiac phase, and controls the display 81 to display. In addition, the display controller 7 assigns the colors determined for each location for each cardiac phase to each location for each cardiac phase, sequentially updates them, and displays them on the display 81.

By thus assigning colors corresponding to the magnitudes of the normalized strain rates to the respective locations on the tomographic image and controlling the display 81 to display the colors, it becomes possible to reduce the influence of variations in strains. Consequently, it becomes possible to appropriately evaluate the diastolic function of the heart.

The contour tracking part 11 may temporally track a membrane contour contained in a region between the endocardial contour and the epicardial contour designated by the operator. For example, the contour tracking part 11 temporally tracks an intermediate membrane contour at an intermediate position between the endocardial contour and the epicardial contour. Through this tracking, the contour tracking part 11 obtains the position of each of the points composing the intermediate membrane for each cardiac phase. The wall-motion-information calculator 21 then uses the position of the intermediate membrane contour at each cardiac phase to calculate wall-motion information. For example, the wall-motion-information calculator 21 obtains a strain in the wall-thickness direction between the endocardium and the intermediate membrane, based on the position of the endocardial contour at each cardiac phase and the position of the intermediate membrane contour at each cardiac phase. Moreover, the wall-motion-information calculator 21 obtains a strain in the wall-thickness direction between the intermediate membrane and the epicardium based on the position of the intermediate membrane contour at each cardiac phase and the position of the epicardial contour at each cardiac phase. Because partial wall-motion information can be obtained by thus tracking the membrane contour contained between the endocardium and the epicardium, it is possible to analyze the myocardial motion in detail. Moreover, a plurality of membrane contours contained between the endocardium and the epicardium may be temporally tracked.

[Modification]

A modification of the ultrasonic imaging apparatus according to the abovementioned embodiment will be described.

(First Modification)

Figure 6:
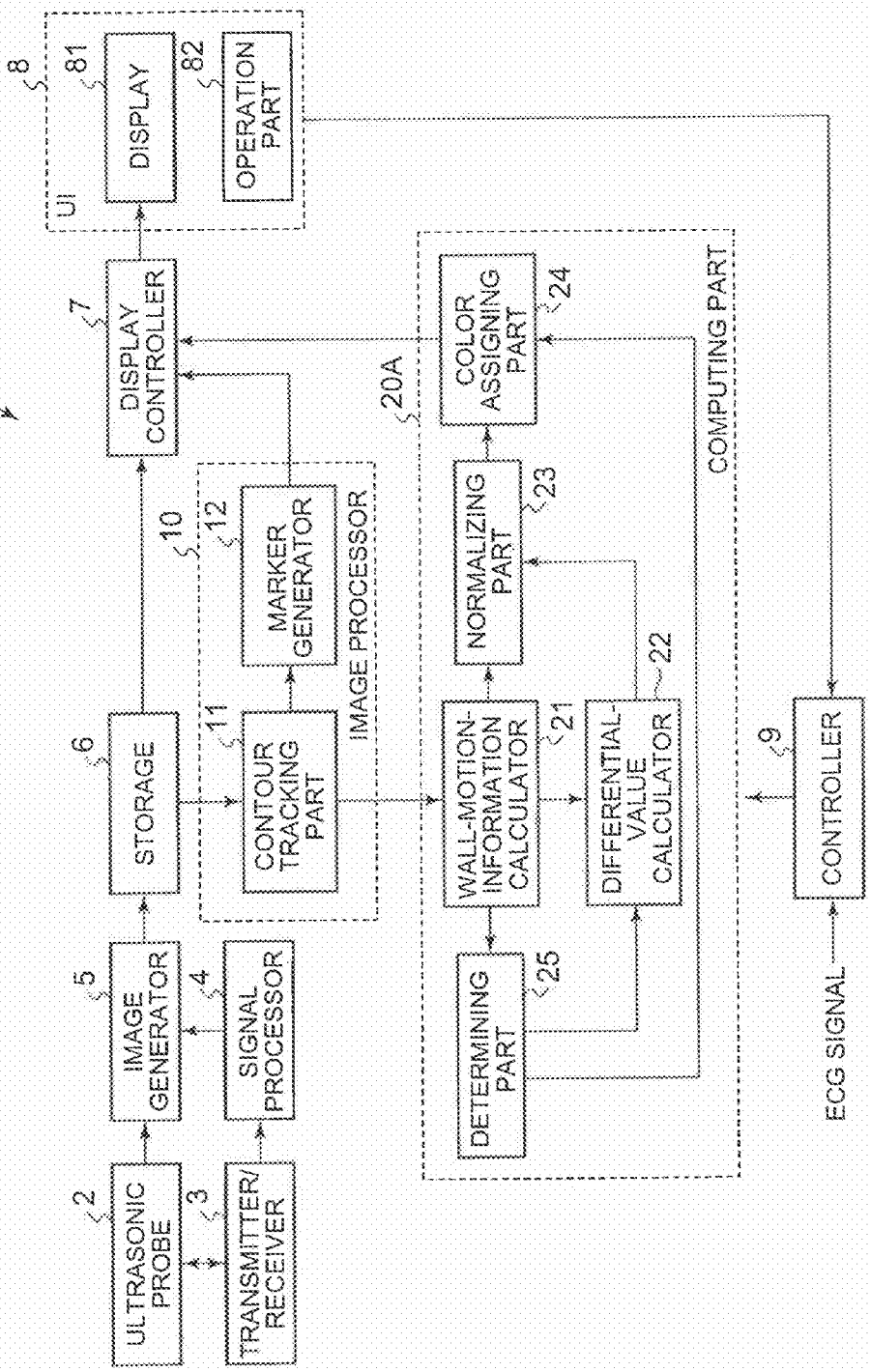
FIG. 6 is a block diagram showing an ultrasonic imaging apparatus according to a first modification.

A first modification will be described with reference to FIG. 6. FIG. 6 is a block diagram illustrating an ultrasonic imaging apparatus according to the first modification. An ultrasonic diagnostic apparatus 1A according to the first modification comprises a computing part 20A instead of the computing part 20. Since the configuration of the ultrasonic diagnostic apparatus 1A other than the computing part 20A is the same as the above-mentioned ultrasonic imaging apparatus 1, a description thereof will be omitted.

Like the computing part 20 according to the above-mentioned embodiment, the computing part 20A includes the wall-motion-information calculator 21, the differential-value calculator 22, the normalizing part 23, and the color determining part 24. The computing part 20A according to the first modification further includes a determining part 25.

The wall-motion-information calculator 21 obtains wall-motion information as in the abovementioned embodiment. As an example, the wall-motion-information calculator 21 obtains a strain $S(t)$ in the wall-thickness direction at every specified interval in the endocardium and epicardium of a heart. That is, the wall-motion-information calculator 21 obtains the strain $S(t)$ at a plurality of locations for each cardiac phase in the endocardium and epicardium of the heart. The wall-motion-information calculator 21 then outputs the strain $S(t)$ in the wall-thickness direction of each location at each cardiac phase to the differential-value calculator 22. In addition, as in the abovementioned embodiment, the wall-motion-information calculator 21 obtains a maximum strain Smax in each location, and outputs the maximum strain Smax of each location to the differential-value calculator 22, the normalizing part 23 and the determining part 25.

The determining part 25 compares the maximum value of the wall-motion information in each location obtained by the wall-motion-information calculator 21 with a preset threshold value, and determines whether the wall-motion information in each location is equal to or more than the threshold value or is less than the threshold value. As an example, the determining part 25 compares the maximum strain Smax in each location obtained by the wall-motion-information calculator 21 with a preset threshold value, and determines whether the maximum strain Smax in each location is equal to or more than the threshold value or is less than the threshold value. The determining part 25 compares the maximum strain Smax with the threshold value for every location, and determines whether the maximum strain Smax is equal to or more than the threshold value or is less than the threshold value for every location. As this threshold value, for example, a reference for determining decrease in cardiac contractility is used.

In this case, if the maximum strain Smax is less than the threshold value, it is possible to determine that the contractility has decreased. If the maximum strain Smax is equal to or more than the threshold value, it is possible to determine that the contractility has not decreased. This threshold value is previously determined and stored in a storage (not shown). The determining part 25 determines whether the maximum strain Smax is equal to or more than the threshold value or is less than the threshold value for every location based on the threshold value stored in the storage. The determining part 25 then outputs the result of the determination using the threshold value to the differential-value calculator 22 and the color determining part 24.

If the maximum strain Smax is equal to or more than the threshold value, it is possible to determine that the contractility at the location has not decreased. Thus, the differential-value calculator 22 obtains a strain rate SR(t) at each cardiac phase, in the location where the maximum strain Smax has been determined to be equal to or more than the threshold value in accordance with the determination by the determining part 25. Then, as in the abovementioned embodiment, the normalizing part 23 obtains a normalized strain rate nSR(t) by dividing the strain rate SR(t) at each cardiac phase in the location where the maximum strain Smax has been determined to be equal to or more than the threshold value by the maximum strain Smax of the location.

Then, the normalizing part 23 outputs the strain rate nSR(t) at each cardiac phase in the location where the maximum strain Smax has been determined to be equal to or more than the threshold value, to the color determining part 24. Then, the color determining part 24 determines a color corresponding to the magnitude of the normalized strain rate nSR(t), as in the abovementioned embodiment. That is, the color determining part 24 assigns a color corresponding to the magnitude of the normalized strain rate nSR(t) to the location where the maximum strain Smax has been determined to be equal to or more than the threshold value. The color determining part 24 then outputs, to the display controller 7, coordinate information of each location at each cardiac phase and information indicating the color determined for each location. The display controller 7 controls the display 81 to display a tomographic image based on the tomographic image data acquired at each cardiac phase, and further controls the display 81 to display in a state where a color corresponding to the magnitude of the normalized strain rate nSR(t) is assigned to the location where the maximum strain Smax is equal to or more than the threshold value.

On the other hand, if the maximum strain Smax is less than the threshold value, it is possible to determine that the contractility at that location has decreased. Thus, the color determining part 24 assigns a specific color for indicating that the contractility has decreased, to the location where the maximum strain Smax is less than the threshold value in accordance with the determination by the determining part 25. For example, the color determining part 24 assigns a specific color that is different from the color assigned for the abovementioned normalized strain rate nSR(t), to the location where the contractility has decreased (location where the maximum strain Smax is less than the threshold value). Then, the color determining part 24 outputs, to the display controller 7, coordinate information of the location where the maximum strain Smax is less than the threshold value and information indicating the specific color determined for that location. The display controller 7 controls the display 81 to display a tomographic image based on the tomographic image data acquired at each cardiac phase, and further controls the display 81 to display in a state where the specific color is assigned to the location where the maximum strain Smax is less than the threshold value.

As described above, the display controller 7 controls the display 81 to display in a state where a color corresponding to the magnitude of the strain rate nSR(t) is assigned to a location where the maximum strain Smax is equal to or more than a threshold value. On the other hand, the display controller 7 controls the display 81 to display in a state where a specific color is assigned to a location where the maximum strain Smax is less than the threshold value. Because the location with the specific color assigned is a location where the contractility has decreased, the operator can refer to the color assigned to each location in a tomographic image to easily grasp the location where the contractility has decreased. Moreover, because a color corresponding to the magnitude of a normalized strain rate nSR(t) is assigned to a location where the maximum strain Smax is equal to or more than the threshold value, the operator can refer to the color to determine decrease or increase in diastolic function.

(Second Modification)

Next, a second modification will be described. An ultrasonic imaging apparatus according to the second modification divides a maximum value or a minimum value of a differential value of wall-motion information in each location by a maximum value of the wall-motion information in each location, thereby obtaining a normalized differential value. As an example, the ultrasonic imaging apparatus according to the second modification obtains a normalized strain rate by dividing the maximum strain rate or the minimum strain rate in each location by the maximum strain in each location.

The wall-motion-information calculator 21 obtains the strain S(t) in each location at each cardiac phase, as in the abovementioned embodiment. In addition, the wall-motion-information calculator 21 obtains the maximum strain Smax for every location between arbitrary cardiac phases, as in the abovementioned embodiment. For example, the wall-motion-information calculator 21 obtains the maximum strain Smax in each location during one cardiac cycle.

The differential-value calculator 22 obtains the strain rate SR(t) in each location at each cardiac phase, as in the abovementioned embodiment. In addition, in the second modification, the differential-value calculator 22 obtains a maximum strain rate SRmax or a minimum strain rate SRmin in every location between arbitrary cardiac phases. For example, the strain-rate calculator 22 obtains the maximum strain rate SRmax or the minimum strain rate SRmin in each location during one cardiac cycle. Then, the differential-value calculator 22 outputs the maximum strain rate SRmax or the minimum strain rate SRmin in each location, to the normalizing part 23.

In the second modification, the normalizing part 23 obtains the normalized strain rate nSR(t) by dividing the maximum strain rate SRmax or the minimum strain rate SRmin in each location by the maximum strain Smax in each location. The normalizing part 23 then outputs the normalized strain rate nSR(t) in each location to the color determining part 24.

The color determining part 24 determines a color corresponding to the magnitude of the normalized strain rate nSR(t) in each location as in the abovementioned embodiment.

Then, the display controller 7 controls the display 81 to display a tomographic image, and further controls the display 81 to display in a state where the color determined for each location is assigned to each location on the tomographic image.

Since cardiac phases at which strain rates reach the maximums vary depending on locations, it is desirable that, for example, the display controller 7 controls the display 81 to display a tomographic image acquired at an average cardiac phase at which the strain rate in each location becomes the maximum or the minimum, and controls the display 81 to display in a state where a color is assigned to each location on that tomographic image.

Moreover, the display controller 7 may control the display 81 to display the tomographic image acquired at the cardiac phase at which the strain rate in an arbitrary location becomes the maximum or the minimum, and control the display 81 to display in a state where a color is assigned to each location on that tomographic image. Further, the display controller 7 may control the display 81 to display the tomographic image acquired at an arbitrary cardiac phase, and control the display 81 to display in a state where a color is assigned to each location on that tomographic image. An arbitrary location or an arbitrary cardiac phase may be designated by the operator using the operation part 82, or may be preset in the display controller 7.

(Third Modification)

Next, a third modification will be described. In the abovementioned embodiment etc., an endocardial contour and an epicardial contour on a 2-dimensional plane are tracked based on tomographic image data as a 2-dimensional image, and wall-motion information is obtained. An ultrasonic imaging apparatus according to the third modification tracks a 3-dimensional endocardial contour and a 3-dimensional epicardial contour based on volume data as a 3-dimensional image, thereby obtaining wall-motion information.

The ultrasonic imaging apparatus according to the third modification acquires volume data of a heart for each cardiac phase, by conducting volume scan using the ultrasonic probe 2 and the transmitter/receiver 3. Then, the image generator 5 performs MPR processing on the volume data acquired at a preset cardiac phase (for example, a cardiac phase at which an R-wave has been detected), thereby generating MPR image data in an arbitrary cross section. For example, the image generator 5 performs MPR processing on the volume data, thereby obtaining MPR image data in a plurality of different cross sections, for each of the cross sections. As an example, the image generator 5 generates two MPR image data in cross sections orthogonal to each other. For example, the image generator 5 generates an apical 4 chamber image (4C) and an apical 2 chamber image (2C) in a long-axis cross section along the long-axis direction of the heart. The long-axis cross section may be preset in the image generator 5, or may be designated by the operator using the operation part 82. The MPR image data generated by the image generator 5 is stored in the storage 6. The display controller 7 may retrieve MPR image data stored in the storage 6 and control the display 81 to display an MPR image based on the MPR image data. For example, the display controller 7 controls the display 81 to display the apical 4 chamber image (4C) and the apical 2 chamber image (2C).

Then, the operator designates the endocardial contour and epicardial contour shown in the tomographic image by using the operation part 82. As an example, the operator uses the operation part 82 to designate the endocardial contour and epicardial contour shown in the apical 4 chamber image and designate the endocardial contour and epicardial contour represented in the apical 2 chamber image. Thus, with reference to the MPR image in the long-axis cross section of the heart, the 2-dimensional endocardial contour and the 2-dimensional epicardial contour in the long-axis cross section are designated. Then, the 2-dimensional endocardial contour and the 2-dimensional epicardial contour are outputted from the user interface (UI) 8 to the image processor 10. The contour tracking part 11 obtains the position of a 3-dimensional endocardial contour by spatially interpolating the endocardial contour based on the 2-dimensional endocardial contour designated in the apical 4 chamber image (4C) and the 2-dimensional endocardial contour designated in the apical 2 chamber image (2C). Moreover, the contour tracking part 11 obtains the position of a 3-dimensional epicardial contour by spatially interpolating the epicardial contour based on the 2-dimensional epicardial contour obtained based on the apical 4 chamber image (4C) and the 2-dimensional epicardial contour obtained based on the apical 2 chamber image (2C).

As described above, the contour tracking part 11 obtains the position of the endocardial contour at each depth in the long-axis direction, based on the endocardial contour defined in the long-axis cross section. Consequently, the position of the 3-dimensional endocardial contour is obtained. Similarly, the contour tracking part 11 obtains the position of the epicardial contour at each depth in the long-axis direction, based on the epicardial contour defined in the long-axis cross section. Consequently, the position of the 3-dimensional epicardial contour is obtained.

Moreover, the image generator 5 may generate MPR image data in the long-axis cross section and generate MPR image data in a short-axis cross section (C plane) along a direction orthogonal to the long-axis direction (a short-axis direction). For example, the image generator 5 generates an apical 4 chamber image (4C) and an apical 2 chamber image (2C) along the long-axis direction of the heart. Furthermore, the image generator 5 generates MPR image data in a first short-axis cross section at an arbitrary depth along the long-axis direction. Moreover, the image generator 5 generates MPR image data in a second short-axis cross section at another depth. Moreover, the image generator 5 generates MPR image data in a third short-axis cross section at another depth. The MPR image data generated by the image generator 5 are stored in the storage 6. The short-axis cross section at each depth may be preset in the image generator 5. Otherwise, the operator may designate the positions of the short-axis cross sections by using the operation part 82. The display controller 7 controls the display 81 to display the apical 4 chamber image, the apical 2 chamber image, an MPR image in the first short-axis cross section, an MPR image in the second short-axis cross section, and an MPR image in the third short-axis cross section.

Then, the operator designates the endocardial contour and the epicardial contour shown in the tomographic image by using the operation part 82. As an example, the operator uses the operation part 82 to designate the endocardial contour and the epicardial contour shown in the apical 4 chamber image and the endocardial contour and the epicardial contour shown in the apical 2 chamber image. Furthermore, the operator uses the operation part 82 to designate the endocardial contour and the epicardial contour shown in the MPR image in the first short-axis cross section. Moreover, the operator uses the operation part 82 to designate the endocardial contour and the epicardial contour shown in the MPR image in the second short-axis cross section. Moreover, the operator uses the operation part 82 to designate the endocardial contour and the epicardial contour shown in the MPR image in the third short-axis cross section. Thus, with reference to the MPR image in the long-axis cross section of the heart, the 2-dimensional endocardial contour and the 2-dimensional epicardial contour in the long-axis cross section are designated. Moreover, with reference to the MPR images in the short-axis cross sections of the heart, the 2-dimensional endocardial contour and the 2-dimensional epicardial contour in the short-axis cross section are designated. Then, the 2-dimensional endocardial contour and the 2-dimensional epicardial contour are outputted from the user interface (UI) 8 to the image processor 10. The contour tracking part 11 obtains the position of a 3-dimensional endocardial contour by spatially interpolating the endocardial contour, based on the 2-dimensional endocardial contours designated in the apical 4 chamber image (4C), the apical 2 chamber image (2C), the MPR image in the first short-axis cross section, the MPR image in the second short-axis cross section, and the MPR image in the third short-axis cross section. As for the 3-dimensional epicardial contour, the contour tracking part 11 obtains the position of a 3-dimensional epicardial contour by spatially interpolating the epicardial contour based on the 2-dimensional epicardial contours designated in the respective images.

The 3-dimensional endocardial contour and the 3-dimensional epicardial contour obtained through the interpolation process are set in the contour tracking part 11 as initial contours. The contour tracking part 11 then tracks the position of the 3-dimensional endocardial contour and the position of the 3-dimensional epicardial contour set as the initial contours, by conducting pattern matching using speckle patterns for the volume data acquired at different times. Through this pattern matching, the position of the 3-dimensional endocardial contour and the position of the 3-dimensional epicardial contour at each cardiac phase are obtained.

The wall-motion-information calculator 21 obtains wall-motion information such as strain and displacement at each cardiac phase, based on coordinate information of each of the points composing the 3-dimensional endocardial contour at each cardiac phase and coordinate information of each of the points composing the 3-dimensional epicardial contour at each cardiac phase, as in the abovementioned embodiment. The differential-value calculator 22 then obtains temporal differentiation of the wall-motion information, and the normalizing part 23 divides a differential value of the wall-motion information by the maximum value of the wall-motion information to normalize the differential value. The color determining part 24 determines a color corresponding to the magnitude of the normalized differential value.

The display controller 7 controls the display 81 to display an MPR image at each cardiac phase, for each cardiac phase. For example, the display controller 7 controls the display 81 to display an apical 4 chamber image (4C) and an apical 2 chamber image (2C) at each cardiac phase, for each cardiac phase. Moreover, the display controller 7 controls the display 81 to display an MPR image in the first short-axis cross section, an MPR image in the second short-axis cross section and an MPR image in the third short-axis cross section, for each cardiac phase. Moreover, the marker generator 12 generates a marker indicating the endocardial contour at each cardiac phase and a marker indicating the epicardial contour at each cardiac phase. The display controller 7 controls the display 81 to sequentially display the marker indicating the endocardial contour at each cardiac phase and the marker indicating the epicardial contour at each cardiac phase in the superimposed state on each MPR image at each cardiac phase. In addition, as in the abovementioned embodiment, the display controller 7 assigns a color corresponding to the magnitude of a normalized differential value to a region between the endocardium and the epicardium, and controls the display 81 to display it in the superimposed state on the MPR image.

In the abovementioned embodiment etc., the computing part 20 obtains a strain and a strain rate in the wall-thickness direction as wall-motion information. Such information is an example, and the computing part 20 may obtain a strain and a strain rate in the circumferential direction as wall-motion information. Moreover, the computing part 20 may obtain rotation, twist or torsion of the myocardium.

Figure 7:
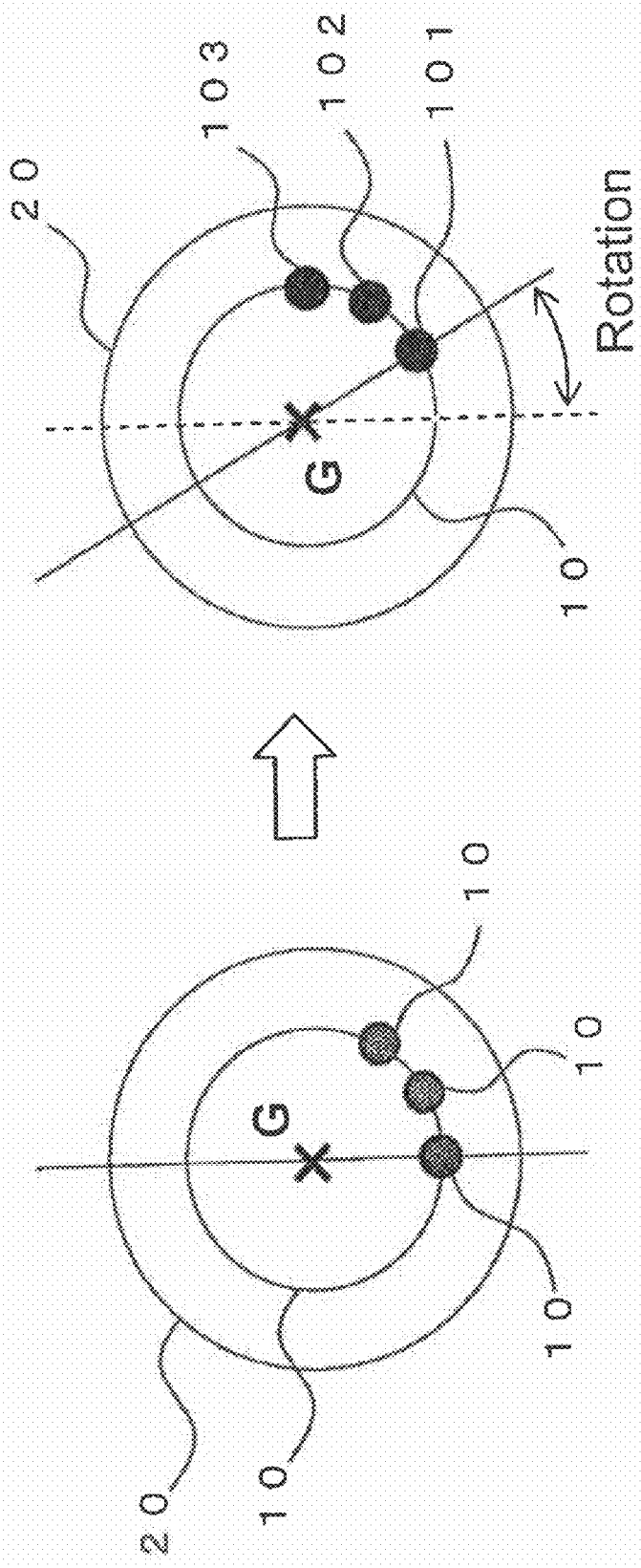
FIG. 7 is a view schematically showing an endocardial contour and an epicardial contour.

Here, as another example of the wall-motion information, rotation, twist and torsion will be described. Firstly, rotation will be described with reference to FIG. 7. FIG. 7 is a view schematically showing the contour of an endocardium and the contour of an epicardium. The wall-motion-information calculator 21 obtains a rotation angle, based on the point 101 on the endocardium 100 at a certain cardiac phase and a point 100A on the endocardium 100 as a result of tracking the point 101. To be specific, the wall-motion-information calculator 21 obtains a gravity center G of the endocardium 100 obtained by the contour tracking part 11. The wall-motion-information calculator 21 obtains the angle between the point 101 and the point 101A with the gravity center G as the center of rotation, and defines the angle as the rotation angle. Furthermore, the wall-motion-information calculator 21 obtains the maximum value of the absolute value of the rotation angle between arbitrary cardiac phases. For example, the wall-motion-information calculator 21 obtains the maximum value of the absolute value of the rotation angle during one heartbeat designated by the operator. The differential-value calculator 22 then obtains the differential value of the rotation angle by conducting temporal differentiation of the rotation angle. The temporal differentiation of the rotation angle is defined as Rotation Rate.

The normalizing part 23 divides the differential value of the rotation angle at each cardiac phase by the maximum value of the absolute value of the rotation angle, thereby obtaining a normalized differential value. The wall-motion-information calculator 21 may obtain the rotation angle between another point 102 on the endocardium 100 and a point 102A as a result of tracking the point 102. Similarly, the wall-motion-information calculator 21 may obtain the rotation angle between a point 103 on the endocardium 100 and a point 103A as a result of tracking the point 103. In addition, the wall-motion-information calculator 21 may obtain the rotation angle between a point on the epicardium 200 and a point as a result of tracking the point. As in the abovementioned embodiment etc., the color determining part 24 determines a color corresponding to the magnitude of the normalized differential value (Rotation Rate). Then, the display controller 7 assigns the color determined by the color determining part 24 to each location of the myocardium on the tomographic image at each cardiac phase, and controls the display 81 to display it.

Figure 8:
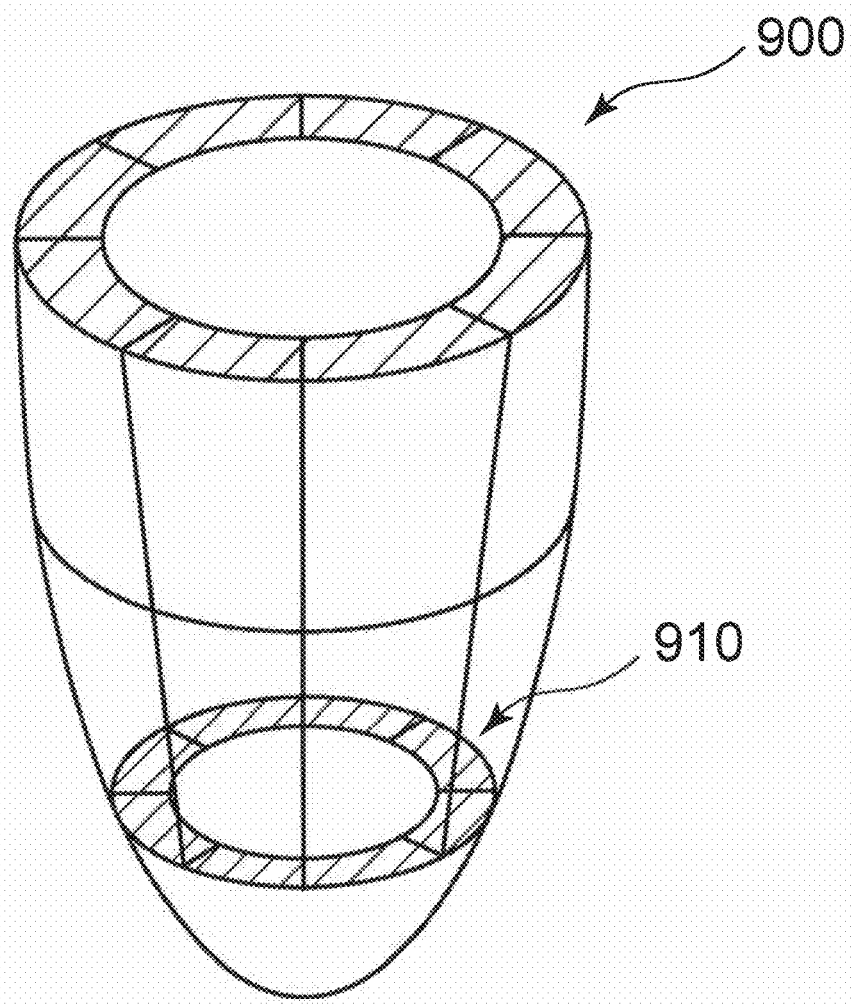
FIG. 8 is a view schematically showing an endocardial contour and an epicardial contour.

As another example of wall-motion information, twist will be described with reference to FIG. 8. FIG. 8 is a view schematically showing the contour of an endocardium and the contour of an epicardium. The difference between the rotation angle on a short-axis cross section 900 to become a reference and the rotation angle on another short-axis cross section 910 is defined as twist. The wall-motion-information calculator 21 obtains the rotation angle on the short-axis cross section 900 to become a reference and the rotation angle on the arbitrary short-axis cross section 910, based on a 3-dimensional contour of the endocardium and a 3-dimensional contour of the epicardium at each cardiac phase. Furthermore, the wall-motion-information calculator 21 obtains the difference between the rotation angle on the arbitrary short-axis cross section 910 and the rotation angle on the short-axis cross section 900 to become a reference, thereby obtaining twist in the short-axis cross section 910. The position of the short-axis cross section 900 to become a reference and the position of the arbitrary short-axis Cross section 910 may be preset in the wall-motion-information calculator 21, or may be designated by the operator using the operation part 82.

Assuming the value of twist in a reference short-axis cross section is Twist(0), Twist(i), which is twist in an $i^{th}$ short-axis cross section, can be expressed by the following expression:

$$\text{Twist}(i) = \text{Rotation}(i) - \text{Rotation}(0) [\deg]$$

Furthermore, the wall-motion-information calculator 21 obtains the maximum value of the twist in the short-axis cross section 910 between arbitrary cardiac phases. For example, the wall-motion-information calculator 21 obtains the maximum value of the twist in the short-axis cross section 910 during one heartbeat designated by the operator. Then, the differential-value calculator 22 performs temporal differentiation of the twist in the short-axis cross section 910 to obtain the differential value of the twist. The temporal differentiation of the twist is defined as Twist Rate.

The normalizing part 23 divides the temporal differentiation of twist at each cardiac phase by the maximum value of the twist, thereby obtaining a normalized differential value. Then, as in the abovementioned embodiment etc., the color determining part 24 determines a color corresponding to the magnitude of the normalized differential value (Twist Rate). The display controller 7 assigns the color determined by the color determining part 24 to each location of the myocardium on a tomographic image at each cardiac phase, and controls the display 81 to display it.

Figure 9:
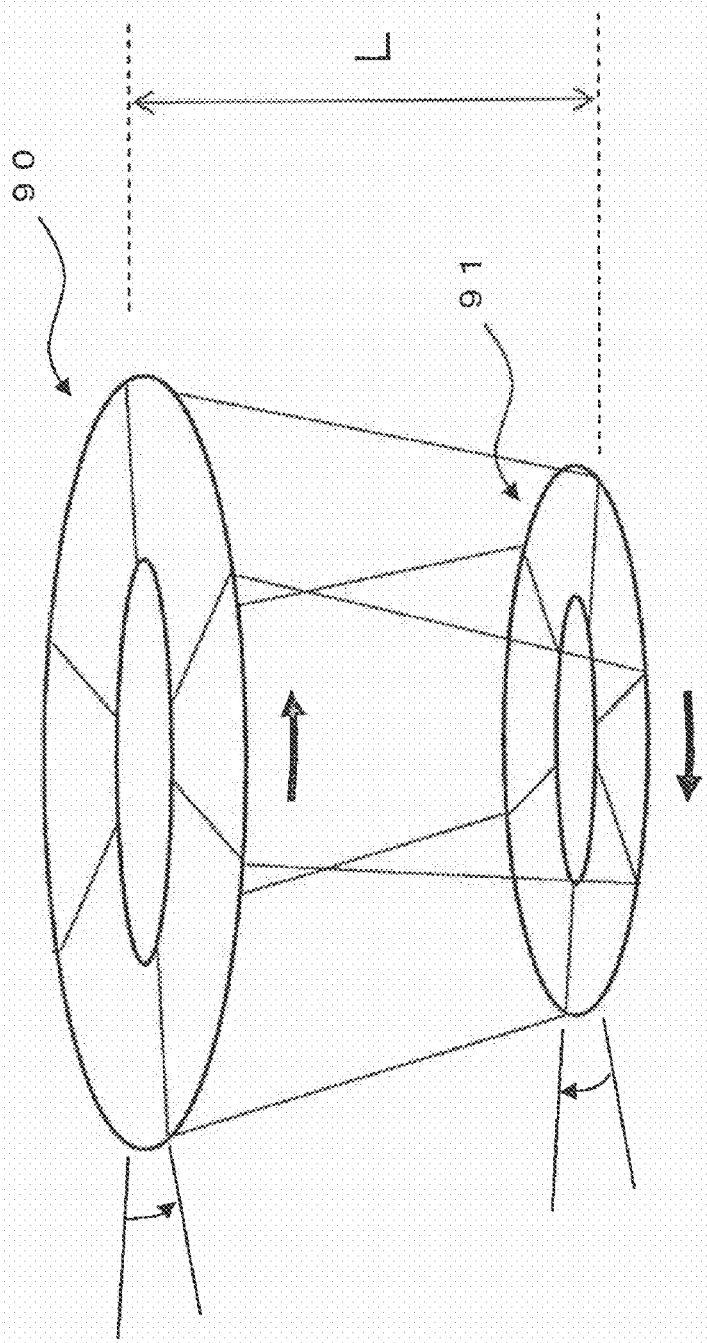
FIG. 9 is a view schematically showing an endocardial contour and an epicardial contour.

Moreover, as another example of the wall-motion information, torsion will be described with reference to FIG. 9. FIG. 9 is a view schematically showing the contour of an endocardium and the contour of an epicardium. A value obtained by dividing twist in the short-axis cross section 910 by a distance L from the reference short-axis cross section 900 to the short-axis cross section 910 is defined as torsion. The wall-motion-information calculator 91 obtains the twist in the arbitrary short-axis cross section 910 with reference to the short-axis cross section 900, and divides the twist by the distance L, thereby obtaining the torsion in the short-axis cross section 910.

That is, Torsion(i) in the $i^{th}$ short-axis cross section can be expressed by the following expression:

$$\text{Torsion}(i) = \text{Twist}(i)/L [\deg/\text{cm}]$$

Furthermore, the wall-motion-information calculator 21 obtains the maximum value of the torsion in the short-axis cross section 910 between arbitrary cardiac phases. For example, the wall-motion-information calculator 21 obtains the maximum value of the torsion in the short-axis cross section 910 during one heartbeat designated by the operator. The differential-value calculator 22 then obtains the differential value of the torsion by conducting temporal differentiation of the torsion in the short-axis cross section 910. The differential value of the torsion is defined as Torsion Rate.

The normalizing part 23 divides the temporal differentiation of the torsion at each cardiac phase by the maximum value of the torsion, thereby obtaining a normalized differential value. The color determining part 24 determines a color corresponding to the magnitude of the normalized differential value (Torsion Rate), as in the abovementioned embodiment etc.

The display controller 7 then assigns the color determined by the color determining part 24 to each location of the myocardium on the tomographic image at each cardiac phase, and controls the display 81 to display.

The maximum value of a differential value of wall-motion information in the diastole indicates the degree of the diastolic function, because it becomes an index indicating the speed of dilation from end systole to early diastole. For example, the differential value of strain indicates dilation velocity, and the larger this value is, the higher the diastolic function is. On the other hand, when the differential value of strain is small, the heart dilates only slowly, indicating that the diastolic function is low. The differential value of wall-motion information is affected by the magnitude of the original wall-motion information to be differentiated. Variations occur in wall-motion information between locations of the myocardium not only in patients with abnormal myocardial motion but also in healthy persons. In this case, it is difficult to evaluate diastolic function by using the differential value of wall-motion information.

Thus, in order to reduce the influence of variations in wall-motion information for differentiation, the differential value is normalized by the maximum value of wall-motion information as in this embodiment. This makes it possible to reduce variations in wall-motion information influencing the differential value, and it becomes possible to appropriately evaluate the diastolic function by using the differential value.

What is claimed is:
1. An ultrasonic image processing apparatus, comprising:
   a contour tracking part configured to receive ultrasonic image data acquired at each time phase by scanning a subject with ultrasonic waves, further receive designation of a contour of a specific tissue shown in an ultrasonic image based on ultrasonic image data acquired at an arbitrary time phase, and obtain a position of each of points composing the contour of the specific tissue in the ultrasonic image data acquired at the each time phase by pattern matching at each time phase based on the ultrasonic image data acquired at the each time phase;
   a computing part configured to obtain motion information of each of parts composing the specific tissue at each time phase based on the position of each of the points composing the contour, obtain a differential value of the motion information of each of the parts at each time phase by differentiating the motion information of each of the parts with respect to time, divide the differential value of the motion information at each of the parts by a maximum value of an absolute value of the motion information at each of the parts to obtain a normalized differential value of the motion information at each of the parts at each time phase, and assign a color corresponding to a magnitude of the normalized differential value of the motion information to each of the parts; and
   a display controller configured to control a display device to display an ultrasonic image based on the ultrasonic image data acquired at the each time phase, and further control to display each of the parts of the specific tissue shown in the ultrasonic image of the each time phase in a color assigned to each of the parts.

2. The ultrasonic image processing apparatus according to claim 1, wherein:

the computing part compares the maximum value of the absolute value of the motion information at each of the parts with a preset threshold value, assigns a color corresponding to the magnitude of the normalized differential value of the motion information to a location where the maximum value is equal to or more than the threshold value, and assigns a specific color different from the color corresponding to the magnitude of the normalized differential value of the motion information to a location where the maximum value is less than the threshold value; and the display controller controls to display each of the parts of the specific tissue shown in the ultrasonic image in the color assigned to each of the parts in accordance with color assignment by the computing part.

3. The ultrasonic image processing apparatus according to claim 1, further comprising:

a marker generator configured to generate a marker indicating the contour of the specific tissue of the each time phase obtained by the contour tracking part, wherein:

the display controller controls the display device to display the ultrasonic image of the each time phase, and further controls the display device to display the marker of the each time phase in a superimposed state on the position of the contour of the specific tissue shown in the ultrasonic image.

4. The ultrasonic image processing apparatus according to claim 1, wherein:

the computing part obtains a strain of each of the parts composing the specific tissue at each time phase as the motion information based on the position of each of the points composing the contour, obtains a strain rate indicating a temporal change rate of the strain at each of the parts at each time phase by differentiating the strain of each of the parts with respect to time, divides the strain rate at each of the parts by a maximum value of an absolute value of the strain at each of the parts to obtain a normalized strain rate at each of the parts at each time phase, and assigns a color corresponding to a magnitude of the normalized strain rate to each of the parts.

5. A method for processing an ultrasonic image, comprising:

acquiring ultrasonic image data acquired at each time phase by scanning a subject with ultrasonic waves;

receiving designation of a contour of a specific tissue shown in an ultrasonic image based on ultrasonic image data acquired at an arbitrary time phase, and obtaining a position of each of points composing the contour of the specific tissue in the ultrasonic image data acquired at the each time phase by pattern matching at each time phase based on the ultrasonic image data acquired at the each time phase;

obtaining motion information of each of parts composing the specific tissue at each time phase based on the position of each of the points composing the contour;

obtaining a differential value of the motion information of each of the parts at each time phase by differentiating the motion information of each of the parts with respect to time;

dividing the differential value of the motion information at each of the parts by a maximum value of an absolute value of the motion information at each of the parts to obtain a normalized differential value of the motion information at each of the parts at each time phase;

assigning a color corresponding to a magnitude of the normalized differential value of the motion information to each of the parts;

displaying an ultrasonic image based on the ultrasonic image data acquired at the each time phase; and displaying each of the parts of the specific tissue shown in the ultrasonic image of the each time phase in a color assigned to each of the parts.

6. The method for processing an ultrasonic image according to claim 5, wherein:

in the color assignment, the maximum value of the absolute value of the motion information at each of the parts is compared with a preset threshold value, a color corresponding to the magnitude of the normalized differential value of the motion information is assigned to a location where the maximum value is equal to or more than the threshold value, and a specific color different from the color corresponding to the magnitude of the normalized differential value of the motion information is assigned to a location where the maximum value is less than the threshold value; and each of the parts of the specific tissue shown in the ultrasonic image is displayed in the color assigned to each of the parts in accordance with the color assignment.

7. The method for processing an ultrasonic image according to claim 5, wherein:

a marker indicating the contour of the specific tissue of the each time phase is generated; and the ultrasonic image of the each time phase is displayed, and further the marker of the each time phase is displayed in a superimposed state on the position of the contour of the specific tissue shown in the ultrasonic image.

* * * * *